United States Patent
Wampler et al.

(10) Patent No.: US 12,049,443 B2
(45) Date of Patent: Jul. 30, 2024

(54) SYNTHESIS OF CONJUGATED DIENE PHEROMONES AND RELATED COMPOUNDS

(71) Applicant: Provivi, Inc., Santa Monica, CA (US)

(72) Inventors: Keith M. Wampler, Santa Monica, CA (US); Choon Woo Lee, Santa Monica, CA (US); David Rozzell, Santa Monica, CA (US)

(73) Assignee: PROVIVI, INC., Santa Monica, CA (US)

(*) Notice: Subject to any disclaimer, the term of this patent is extended or adjusted under 35 U.S.C. 154(b) by 211 days.

(21) Appl. No.: 17/312,374

(22) PCT Filed: Dec. 10, 2019

(86) PCT No.: PCT/US2019/065519
§ 371 (c)(1),
(2) Date: Jun. 9, 2021

(87) PCT Pub. No.: WO2020/123534
PCT Pub. Date: Jun. 18, 2020

(65) Prior Publication Data
US 2022/0017449 A1  Jan. 20, 2022

Related U.S. Application Data

(60) Provisional application No. 62/777,680, filed on Dec. 10, 2018.

(51) Int. Cl.
| C07C 67/343 | (2006.01) |
| B01J 31/24 | (2006.01) |
| C07C 45/68 | (2006.01) |

(52) U.S. Cl.
CPC ......... *C07C 67/343* (2013.01); *B01J 31/2442* (2013.01); *C07C 45/68* (2013.01); *B01J 2531/821* (2013.01)

(58) Field of Classification Search
CPC ............. B01J 2531/821; B01J 31/2442; C07C 45/68; C07C 47/21; C07C 67/343; C07C 69/145; G02B 27/646; G03B 13/36; G03B 17/12; G03B 2205/0007; G03B 2205/0046; G03B 5/02; H02K 33/18; H04N 23/55; C07F 15/0046
See application file for complete search history.

(56) References Cited

U.S. PATENT DOCUMENTS

| 6,794,534 | B2 | 9/2004 | Grubbs et al. |
| 7,205,424 | B2 | 4/2007 | Nolan |
| 7,834,144 | B2 | 11/2010 | Peretz et al. |
| 2012/0237552 | A1 | 9/2012 | Moreno et al. |
| 2016/0145204 | A1 | 5/2016 | Johns et al. |
| 2017/0137365 | A1 | 5/2017 | Wampler et al. |
| 2017/0137447 | A1 | 5/2017 | Dufour et al. |

FOREIGN PATENT DOCUMENTS

| CN | 102884070 A | 1/2013 |
| CN | 108473390 A | 8/2018 |
| JP | 2013522351 A | 6/2013 |
| WO | 2000015339 A1 | 3/2000 |
| WO | 0100553 A1 | 1/2001 |
| WO | 01/36368 A2 | 5/2001 |
| WO | 2011117571 A1 | 9/2011 |
| WO | 2013029079 A1 | 3/2013 |
| WO | 2016001383 A1 | 1/2016 |
| WO | 2017087710 A2 | 5/2017 |
| WO | 2018034931 A1 | 2/2018 |
| WO | 2018038928 A1 | 3/2018 |
| WO | 2018150379 A2 | 8/2018 |
| WO | 2018154244 A1 | 8/2018 |
| WO | WO2018154244 | * 8/2018 |

OTHER PUBLICATIONS

WO2018154244 translation (Year: 2018).*
Sytniczuk et al. (Fishing for the right catalysts for the cross-metathesis reaction of methyl oleate with 2-methyl-2-butene, Catalysis Science and Technology, 7, pp. 1284-1296 and cover page, Published 2017) (Year: 2017).*
Caijo et al. (Screening of a selection of commercially available homogeneous Ru-catalysts in valuable olefin metathesis transformations, Catal. Sci. Technol., pp. 429-435, Published 2013) (Year: 2013).*
Umicore M Catalysts, Alkene Metathesis Catalysts, Umicore Precious Metals Chemistry, 2015, 6 pages.
De Figueiredo et al., "Bidirectional, Organocatalytic Synthesis of Lepidopteran Sex Pheromones," The Journal of Organic Chemistry, vol. No. 72, No. 2, Jan. 1, 2007, pp. 640-642.
Application No. EP19897271.3, Extended European Search Report, Mailed on Apr. 4, 2022, 7 pages.
Gessler et al., "Synthesis and Metathesis Reactions of a Phosphine-Free Dihydroimidazole Carbene Ruthenium Complex," Tetrahedron Letters, vol. 41, No. 51, Dec. 16, 2000, pp. 9973-9976.
He et al., "Studies Towards the Synthesis of the Antibiotic Tetrodecamycin," Synlett, vol. 29, No. 8, 2018, pp. 1117-1121.

(Continued)

*Primary Examiner* — Yevgeny Valenrod
*Assistant Examiner* — Blaine G Doletski
(74) *Attorney, Agent, or Firm* — Kilpatrick Townsend & Stockton LLP

(57) ABSTRACT

Methods for preparing conjugated dienes are described. An α,β-unsaturated E olefin intermediate may be prepared via cross-metathesis using a catalyst comprising a transition metal (e.g., ruthenium), a first carbene ligand (e.g., a substituted indenylidene) and an N-heterocyclic carbene ligand (e.g., an imidazolidinylidene). The catalyst further includes a phenylphosphine ligand, a tri(isopropoxy)phosphine ligand, a dimethylsulfoxide ligand, an acetonitrile ligand, or a pyridine ligand. Following the cross metathesis-step, the α,β-unsaturated aldehyde intermediate may be converted to the conjugated diene product via reaction with a phosphonium ylide. Products obtained via the methods of the disclosure include (7E,9Z)-dodeca-7,9-dien-1-yl acetate, a pheromone produced by *Lobesia botrana* (European grapevine moth), and other insect pheromones.

19 Claims, No Drawings

(56) References Cited

OTHER PUBLICATIONS

Hodgson et al., "Convergent and Stereoselective Synthesis of Trisubstituted E-Alkenyl Bromides and Iodides via β-Oxido Phosphonium Ylides," Journal of the American Chemical Society, vol. 130, No. 49, 2008, pp. 16500-16501.
Murelli et al., "Ruthenium-Catalyzed Tandem Cross-Metathesis/Wittig Olefination: Generation of Conjugated Dienoic Esters from Terminal Olefins," Organic Letters, vol. 9, No. 9, 2007, pp. 1749-1752.
Application No. PCT/US2019/065519, International Search Report and Written Opinion, Mailed on Apr. 7, 2020, 14 pages.
Schlosser et al., "Trans-Selective Olefin Syntheses," Angewandte Chemie International Edition, vol. 5, No. 1, Jan. 1966, p. 126 https://doi.org/10.1002/anie.196601261.
Sirasani et al., "Sequencing Cross-Metathesis and Non-Metathesis Reactions to Rapidly Access Building Blocks for Synthesis," Tetrahedron, Elsevier Sience Publishers, Amsterdam, NL, vol. 67, No. 12, Jan. 26, 2011, pp. 2197-2205.
Urbina-Blanco, "Olefin Metathesis Featuring Ruthenium Indenylidene Complexes With a Sterically Demanding Nhc Ligand," Chemistry A European Journal, vol. 17, No. 18, Apr. 26, 2011, pp. 5045-5053.
Chemos GmbH & Co.KG, Acrolein, Safety Data Sheet, Version No. GHS 1.0, Dec. 12, 2022, 15 pages.
Chemos GmbH & Co.KG, Crotonaldehyde, Safety Data Sheet, Version No. GHS 1.0, Jun. 10, 2021, 14 pages.
European Patent Application No. 19897271.3, Third Party Observation, May 14, 2024, 14 pages.

\* cited by examiner

SYNTHESIS OF CONJUGATED DIENE PHEROMONES AND RELATED COMPOUNDS

CROSS-REFERENCE TO RELATED APPLICATION

The present application claims priority to U.S. Provisional Pat. Appl. No. 62/777,680, filed on Dec. 10, 2018, which application is incorporated herein by reference in its entirety.

BACKGROUND OF THE INVENTION

Insect infestation is a primary cause of crop loss throughout the world. A wide variety of chemical pesticides has been relied upon in the past to control insect pests. However, environmental concerns as well as consumer safety concerns have led to the de-registration of many pesticides and a reluctance to use others on agricultural products which are ultimately consumed as food. As a consequence, there is a desire for the development of alternative biological control agents.

Pheromones are chemicals which are secreted outside the body of insects and can be classified according to the type of behavioral reaction they induce. Pheromone classes include aggregation pheromones, sexual pheromones, trail pheromones, and alarm pheromones. Sex pheromones, for example, are typically secreted by insects to attract partners for mating. When pheromones are dispersed on leaves of a crop plant, or in an orchard environment in small quantities over a continuous period of time, pheromone levels reach thresholds that can modify insect behavior. Maintenance of pheromone levels at or above such thresholds can impact insect reproductive processes and reduce mating. Use of pheromones in conjunction with conventional insecticides can therefore reduce the quantity of insecticide required for effective control and can specifically target pest insects while preserving beneficial insect populations. These advantages can reduce risks to humans and the environment and lower overall insect control costs.

Despite these advantages, pheromones are not widely used today because of the high cost of these active ingredients. Even though thousands of insect pheromones have been identified, less than about twenty insect pests worldwide are currently controlled using pheromone strategies, and only 0.05% of global agricultural land employs pheromones. Lepidopteran pheromones, which are naturally occurring compounds, or identical or substantially similar synthetic compounds, are typically characterized by an unbranched aliphatic chain (between 9 and 18 carbon atoms) ending in an alcohol, aldehyde, or acetate functional group and containing up to 3 double bonds in the aliphatic backbone. The preparation of conjugated diene pheromone compounds with control of olefin geometry at both positions remains particularly challenging.

BRIEF SUMMARY OF THE INVENTION

Provided herein are methods for preparing a conjugated diene according to Formula I:

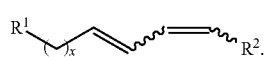

The methods include:
(i) forming a reaction mixture comprising:
an olefin according to Formula V:

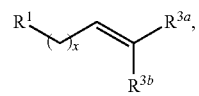

an aldehyde according to Formula IV:

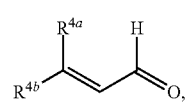

and
a metathesis catalyst comprising a transition metal and (a) a first carbene ligand, (b) an N-heterocyclic carbene ligand, and (c) a phenylphosphine ligand, a tri(isopropoxy)phosphine ligand, a dimethylsulfoxide ligand, an acetonitrile ligand, or a pyridine ligand;
(ii) maintaining the reaction mixture under conditions sufficient to form a metathesis product according to Formula III:

and
(iii) combining the metathesis product according to Formula III with a phosphonium ylide according to Formula II:

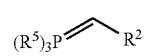

under conditions sufficient to form the conjugated diene according to Formula I, wherein:
$R^1$ is $-OR^{1a}$, $-C(O)OR^{1b}$, or $-C(O)H$,
$R^{1a}$ is H or $C_{1-6}$ acyl,
$R^{1b}$ is H or $C_{1-6}$ alkyl,
$R^2$ is $C_{1-12}$ alkyl,
$R^{3a}$, $R^{3b}$, $R^{4a}$, and $R^{4b}$ are independently H or $C_{1-6}$ alkyl,
each $R^5$ is independently optionally substituted $C_6$-$C_{10}$ aryl, and
subscript x is an integer ranging from 1 to 12.

DETAILED DESCRIPTION OF THE INVENTION

Provided herein are efficient methods for preparation of 1,3-diene products with high control of olefin geometry in the target products and related synthetic intermediates. Terminal alkenes (e.g., oct-7-en-1-yl acetate, obtained via acetylation of oct-7-en-1-ol) and α,β-unsaturated aldehydes (e.g., crotonaldehyde) are converted to conjugated aldehyde intermediates via cross-metathesis employing transition metal catalysts (e.g., a second-generation Grubbs catalyst)

with high selectivity. The cross-metathesis can be conducted with very low catalyst loading. Conjugated aldehyde intermediates can then be carried directly, without isolation, into a Wittig reaction with alkylphosphonium halides to yield the target products with high selectivity. Fractional short-path distillation can be employed to yield purified products (e.g., E,Z-dodecadien-7,9-1-yl acetate) on an industrial scale with a high isomeric purity of (e.g., >87%). One non-limiting embodiment of the methods is shown in Scheme 1.

1.04X, and 1.05X. Thus, "about X" and "around X" are intended to teach and provide written description support for a claim limitation of, e.g., "0.99X."

As used herein, the term "pheromone" refers to a substance, or characteristic mixture of substances, that is secreted and released by an organism and detected by a second organism of the same species or a closely related species. Typically, detection of the pheromone by the second organism promotes a specific reaction, such as a definite

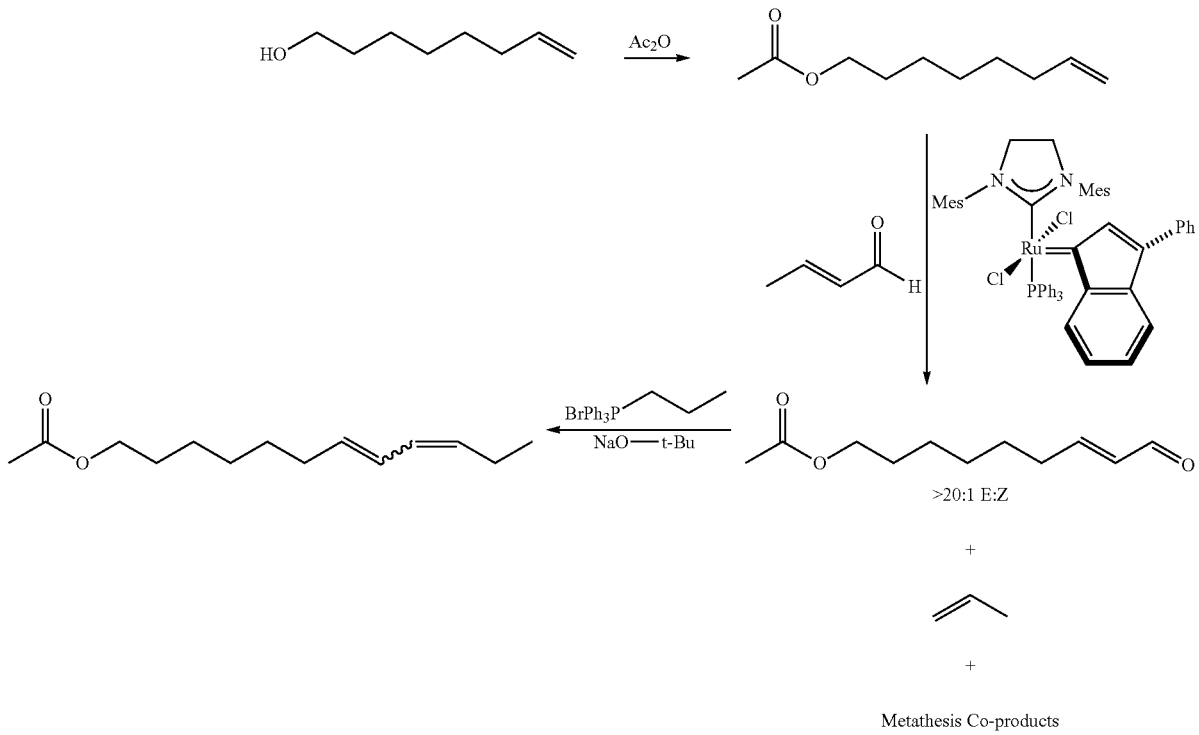

Scheme 1.

I. Definitions

The following definitions and abbreviations are to be used for the interpretation of the invention. The terms "invention" or "present invention" as used herein are non-limiting terms and are not intended to refer to any single embodiment but encompass all possible embodiments.

As used herein, the terms "comprises," "comprising," "includes," "including," "has," "having, "contains," "containing," or any other variation thereof, are intended to embrace a non-exclusive inclusion. A composition, mixture, process, or method that comprises a list of elements is not necessarily limited to only those elements but may include other elements not expressly listed or inherent to such composition, mixture, process, or method. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, and in certain instances, a value from 0.95X to 1.05X, from 0.98X to 1.02X, or from 0.99X to 1.01X. Any reference to "about X" or "around X" specifically indicates at least the values X, 0.95X, 0.96X, 0.97X, 0.98X, 0.99X, 1.01X, 1.02X, 1.03X, behavioral reaction or a developmental process. Insect pheromones, for example, can influence behaviors such as mating and aggregation. Examples of pheromones include, but are not limited to, compounds produced by Lepidoptera (e.g., moths and butterflies belonging to the Geometridae, Noctuidae, Arctiidae, and Lymantriidae families) such as $C_{10}$-$C_{18}$ acetates, $C_{10}$-$C_{18}$ alcohols, $C_{10}$-$C_{18}$ aldehydes, and $C_{17}$-$C_{23}$ polyenes. An "unsaturated pheromone" refers to any pheromone having at least one carbon-carbon double bond.

As used herein, the terms "contacting" and "combining" refer to the process of bringing into contact at least two distinct species such that they can react. It will be appreciated that the resulting reaction product can be produced directly from a reaction between the added reagents or from an intermediate from one or more of the added reagents that can be produced in the reaction mixture.

As used herein, the term "olefin" refers to a straight-chain or branched hydrocarbon compound containing at least one carbon-carbon double bond and derivatives thereof. The olefin can be unsubstituted or substituted with one or more functional groups including alcohol groups, protected alcohol groups, carboxylate groups, and carboxylic acid ester groups. Hydrocarbons having more than one carbon-carbon double bond and derivatives thereof are also referred to as "polyenes." The term "fatty olefin" refers to an olefin having at least four carbon atoms; fatty olefins can have, for example, 4, 6, 8, 10, 12, 14, 16, 18, 20, 22, 24, or 28 carbon atoms. An "olefin derivative" refers to a compound obtained from an olefin starting material (e.g., a fatty olefin starting material). Examples of olefin derivatives include, but are not limited to, unsaturated alcohols, unsaturated alcohol acetates, unsaturated aldehydes, unsaturated fatty acid esters, and polyenes.

As used herein, the term "metathesis reaction" refers to a catalytic reaction which involves the interchange of alkylidene units (i.e., $R_2C=$units) among compounds containing one or more carbon-carbon double bonds (e.g., olefinic compounds) via the formation and cleavage of the carbon-carbon double bonds. Metathesis can occur between two molecules having the same structure (often referred to as self-metathesis) and/or between two molecules having different structures (often referred to as cross-metathesis).

As used herein, the term "metathesis catalyst" refers to any catalyst or catalyst system that catalyzes a metathesis reaction. One of skill in the art will appreciate that a metathesis catalyst can participate in a metathesis reaction so as to increase the rate of the reaction, but is itself not consumed in the reaction. A "ruthenium catalyst" refers to a metathesis catalyst having one or more ruthenium atoms.

As used herein, the term "metathesis product" refers to an olefin containing at least one double bond, the bond being formed via a metathesis reaction.

As used herein, the term "converting" refers to reacting a starting material with at least one reagent to form an intermediate species or a product. The converting can also include reacting an intermediate with at least one reagent to form a further intermediate species or a product.

As used herein, the term "acylating" refers to converting a alcohol group (—OH), to and ester group (—OC(O)R, where R is an alkyl group as described below).

The term "aliphatic" or "aliphatic group," as used herein, refers to a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle" or "cycloaliphatic"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. In some embodiments, "cycloaliphatic" (or "carbocycle") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl, or (cycloalkyl)alkenyl. The term "heteroaliphatic" refers to an aliphatic group wherein at least one carbon atom of the aliphatic group is replaced with a heteroatom (e.g., nitrogen, oxygen, or sulfur, including any oxidized form of nitrogen or sulfur, and any quaternized form of a basic nitrogen).

As used herein, the term "alkyl" is given its ordinary meaning in the art and includes straight-chain alkyl groups and branched-chain alkyl groups. In certain embodiments, a straight chain or branched chain alkyl has about 1-30 carbon atoms in its backbone (e.g., $C_1$-$C_{30}$ for straight chain, $C_3$-$C_{30}$ for branched chain), and alternatively, about 1-20. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkoxy" refers to a moiety —OR wherein R is an alkyl group as defined above.

As used herein, the term "cycloalkyl" refers to a saturated, monocyclic hydrocarbon, bicyclic hydrocarbon, or tricyclic hydrocarbon group that has a single point of attachment to the rest of the molecule. Cycloalkyl groups include alkyl substituted cycloalkyl groups and cycloalkyl substituted alkyl groups. In some embodiments, cycloalkyl rings have from about 3-10 carbon atoms in their ring structure where such rings are monocyclic or bicyclic, and alternatively about 5, 6 or 7 carbons in the ring structure.

As used herein, the term "alkenyl" refers to an alkyl group, as defined herein, having one or more double bonds. The term "heteroalkenyl" refers to an alkenyl group wherein one or more carbon atoms is replaced with a heteroatom (e.g., nitrogen, oxygen, or sulfur, including any oxidized form of nitrogen or sulfur, and any quaternized form of a basic nitrogen).

As used herein, the term "alkynyl" refers to an alkyl group, as defined herein, having one or more triple bonds.

The term "aryl" used alone, or as part of another substituent, refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "aryloxy" refers to a moiety —OR, wherein R is an aryl group as defined above.

The terms "heteroaryl" and "heteroar-," used alone or as part of another substituent, refer to groups having 5 to 10 ring atoms (e.g., monocyclic or bicyclic), in some embodiments 5, 6, 9, or 10 ring atoms. In some embodiments, such rings have 6, 10, or 14 pi electrons shared in a cyclic arrangement; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted.

Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. It should be understood that, when aryl and heteroaryl groups are used as ligands coordinating a metal center, the aryl and heteroaryl groups may have sufficient ionic character to coordinate the metal center. For example, when a heteroaryl group such as pyrrole is used as a nitrogen-containing ligand, as described herein, it should be understood that the pyrrole group has sufficient ionic character (e.g., is sufficiently deprotonated to define a pyrrolyl) to coordinate the metal center. In some cases, the aryl or heteroaryl group may comprise at least one functional group that has sufficient ionic character to coordinate the metal center, such as a biphenolate group, for example.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more heteroatoms (e.g., one to four heteroatoms), as defined above. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl-ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

The terms "halogen" and "halo" are used interchangeably to refer to F, Cl, Br, or I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are generally those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\alpha$; $-(CH_2)_{0-4}OR^\alpha$; $-O(CH_2)_{0-4}R^\alpha$, $-O-(CH_2)_{0-4}C(O)OR^\alpha$; $-(CH_2)_{0-4}CH(OR^\alpha)_2$; $-(CH_2)_{0-4}SR^\alpha$; $-(CH_2)_{0-4}Ph$, which may be substituted with $R^\alpha$; $-(CH_2)_{0-4}O(CH_2)_{0-1}Ph$ which may be substituted with $R^\alpha$; $-CH=CHPh$, which may be substituted with $R^\alpha$; $-(CH_2)_{0-4}O(CH_2)_{0-1}$-pyridyl which may be substituted with $R^\alpha$; $-NO_2$; $-CN$; $-N_3$; $-(CH_2)_{0-4}N(R^\alpha)_2$; $-(CH_2)_{0-4}N(R^\alpha)C(O)R^\alpha$; $-N(R^\alpha)C(S)R^\alpha$; $-(CH_2)_{0-4}N(R^\alpha)C(O)NR^\alpha_2$; $-N(R^\alpha)C(S)NR^\alpha_2$; $-(CH_2)_{0-4}N(R^\alpha)C(O)OR^\alpha$; $-N(R^\alpha)N(R^\alpha)C(O)R^\alpha$; $-N(R^\alpha)N(R^\alpha)C(O)NR^\alpha_2$; $-N(R^\alpha)N(R^\alpha)C(O)OR^\alpha$; $-(CH_2)_{0-4}C(O)R^\alpha$; $-C(S)R^\alpha$; $-(CH_2)_{0-4}C(O)OR^\alpha$; $-(CH_2)_{0-4}C(O)SR^\alpha$; $-(CH_2)_{0-4}C(O)OSiR^\alpha_3$; $-(CH_2)_{0-4}OC(O)R^\alpha$; $-OC(O)(CH_2)_{0-4}SR-SC(S)SR^\alpha$; $-(CH_2)_{0-4}SC(O)R^\alpha$; $-(CH_2)_{0-4}C(O)NR^\alpha_2$; $-C(S)NR^\alpha_2$, $-C(S)SR^\alpha$; $-SC(S)SR^\alpha$, $-(CH_2)_{0-4}OC(O)NR^\alpha_2$; $-C(O)N(OR^\alpha)R^\alpha$; $-C(O)C(O)R^\alpha$; $-C(O)CH_2C(O)R^\alpha$; $-C(NOR^\alpha)R^\alpha$; $-(CH_2)_{0-4}SSR^\alpha$; $-(CH_2)_{0-4}S(O)_2R^\alpha$; $-(CH_2)_{0-4}S(O)_2OR^\alpha$; $-(CH_2)_{0-4}OS(O)_2R^\alpha$; $-S(O)_2NR^\alpha_2$; $-(CH_2)_{0-4}S(O)R^\alpha$; $-N(R^\alpha)S(O)_2NR^\alpha_2$; $-N(R^\alpha)S(O)_2R^\alpha$; $-N(OR^\alpha)R^\alpha$; $-C(NH)NR^\alpha_2$; $-P(O)_2R^\alpha$; $-P(O)R^\alpha_2$; $-OP(O)R^\alpha_2$; $-OP(O)(OR^\alpha)_2$; $SiR^\alpha_3$; $-(C_{1-4}$ straight or branched)alkylene)-O$-N(R^\alpha)_2$; or $-(C_{1-4}$ straight or branched)alkylene)C(O)O$-N(R^\alpha)_2$, wherein each $R^\alpha$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aromatic ring having 0-4 heteroatoms independently selected from nitrogen, oxygen, and sulfur, or, notwithstanding the definition above, two independent occurrences of $R^\alpha$, taken together with their intervening atom(s), form a 3-12-membered saturated, partially unsaturated, or aromatic mono- or bi-cyclic ring having 0-4 heteroatoms independently selected from nitrogen, oxygen, and sulfur, which may be substituted as defined below.

Suitable monovalent substituents on $R^\alpha$ (or the ring formed by taking two independent occurrences of $R^\alpha$ together with their intervening atoms), are independently halogen, $-(CH_2)_{0-2}R^\beta$; -(halo$R^\beta$); $-(CH_2)_{0-2}OH$; $-(CH_2)_{0-2}OR^\beta$; $-(CH_2)_{0-2}CH(OR^\beta)_2$; $-O(halo R^\beta)$; $-CN$; $-N_3$; $-(CH_2)_{0-2}C(O)R^\beta$; $-(CH_2)_{0-2}C(O)OH$; $-(CH_2)_{0-2}C(O)OR^\beta$; $-(CH_2)_{0-2}SR^\beta$; $-(CH_2)_{0-2}SH$; $-(CH_2)_{0-2}NH_2$; $-(CH_2)_{0-2}NHR^\beta$; $-(CH_2)_{0-2}NR^\beta_2$; $-NO_2$; $SiR^\beta_3$; $-OSiR^\beta_3$; $-C(O)SR^\beta$; $-(C_{1-4}$ straight or branched alkylene)C(O)OR$^\beta$; or $-SSR^\beta$; wherein each $R^\beta$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aromatic ring having 0-4 heteroatoms independently selected from nitrogen, oxygen, and sulfur. Suitable divalent substituents on a saturated carbon atom of $R^\alpha$ include =O and =S.

Suitable divalent substituents on a saturated carbon atom of an "optionally substituted" group include the following:

=O; =S; =NNR$^\gamma_2$; =NNHC(O)R$^\gamma$; =NNHC(O)OR$^\gamma$; =NNHS(O)$_2$R$^\gamma$; =NR$^\gamma$; =NOR$^\gamma$; —O(C(R$^\gamma_2$))$_{2-3}$O—; or —S(C(R$^\gamma_2$))$_{2-3}$S—; wherein each independent occurrence of R$^\gamma$ is selected from hydrogen, C$_{1-6}$ aliphatic which may be substituted as defined below, or an unsubstituted 5-6-membered saturated, partially unsaturated, or aromatic ring having 0-4 heteroatoms independently selected from nitrogen, oxygen, and sulfur. Suitable divalent substituents that are bound to vicinal substitutable carbons of an "optionally substituted" group include: —O(CR$^\beta_2$)$_{2-3}$O—, wherein each independent occurrence of R$^\beta$ is selected from hydrogen, C$_{1-6}$ aliphatic which may be substituted as defined below, or an unsubstituted 5-6-membered saturated, partially unsaturated, or aromatic ring having 0-4 heteroatoms independently selected from nitrogen, oxygen, and sulfur.

Suitable substituents on the aliphatic group of R$^\gamma$ include halogen, —R$^\delta$, -(haloR$^\delta$), —OH, —OR$^\delta$, —O(haloR$^\delta$), —CN, —C(O)OH, —C(O)OR$^\delta$, —NH$_2$, —NHR$^\delta$, —NR$^\delta_2$, or —NO$_2$, wherein each R$^\delta$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aromatic ring having 0-4 heteroatoms independently selected from nitrogen, oxygen, and sulfur.

Suitable substituents on a substitutable nitrogen of an "optionally substituted" group include —R$^\varepsilon$, —NR$^\varepsilon_2$, —C(O)R$^\varepsilon$, —C(O)OR$^\varepsilon$, —C(O)C(O)R$^\varepsilon$, —C(O)CH$_2$C(O) R$^\varepsilon$, —S(O)$_2$R$^\varepsilon$, —S(O)$_2$NR$^\varepsilon_2$, —C(S)NR$^\varepsilon_2$, —C(NH)NR$^\varepsilon_2$, or —N(R$^\varepsilon$)S(O)$_2$R$^\varepsilon$; wherein each R$^\varepsilon$ is independently hydrogen, C$_{1-6}$ aliphatic which may be substituted as defined below, unsubstituted —OPh, or an unsubstituted 5-6-membered saturated, partially unsaturated, or aromatic ring having 0-4 heteroatoms independently selected from nitrogen, oxygen, and sulfur, or, notwithstanding the definition above, two independent occurrences of W, taken together with their intervening atom(s) form an unsubstituted 3-12-membered saturated, partially unsaturated, or aromatic mono- or bicyclic ring having 0-4 heteroatoms independently selected from nitrogen, oxygen, and sulfur.

Suitable substituents on the aliphatic group of W are independently halogen, —R$^\delta$, -(haloR$^\delta$), —OH, —OR$^\delta$, —CN, —C(O)OH, —C(O)OR$^\delta$, —NH$_2$, —NHR$^\delta$, —NR$^\delta_2$, or —NO$_2$, wherein each R$^\delta$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aromatic ring having 0-4 heteroatoms independently selected from nitrogen, oxygen, and sulfur.

The term "substituted" is generally meant to include all permissible substituents of organic compounds, "permissible" being in the context of the chemical rules of valence known to those of ordinary skill in the art. In some cases, "substituted" may generally refer to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group. In a broad aspect, permissible substituents include acyclic and cyclic, branched and unbranched, carbocyclic and heterocyclic, aromatic and nonaromatic substituents of organic compounds. Illustrative substituents include, for example, those described herein. Permissible substituents can be one or more and the same or different for appropriate organic compounds. For example, a substituted alkyl group may be CF3. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, carboxamido, nitro, acyloxy, aminoalkyl, alkylaminoaryl, alkylaryl, alkylaminoalkyl, alkoxyaryl, arylamino, arylalkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like.

II. Methods for Conjugated Diene Synthesis

Provided herein are methods for preparing a conjugated diene according to Formula I:

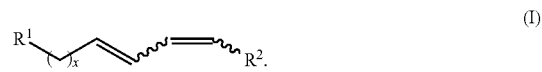

The methods include:
(i) forming a reaction mixture comprising:
an olefin according to Formula V:

an aldehyde according to Formula IV:

and
a metathesis catalyst comprising a transition metal and (a) a first carbene ligand, (b) an N-heterocyclic carbene ligand, and (c) a phenylphosphine ligand, a tri(isopropoxy)phosphine ligand, a dimethylsulfoxide ligand, an acetonitrile ligand, or a pyridine ligand;
(ii) maintaining the reaction mixture under conditions sufficient to form a metathesis product according to Formula III:

and (iii) combining the metathesis product according to Formula III with a phosphonium ylide according to Formula II:

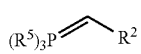
(II)

under conditions sufficient to form the conjugated diene according to Formula I, wherein:

$R^1$ is —$OR^{1a}$, —$C(O)OR^{1b}$, or —$C(O)H$, $R^{1a}$ is H or $C_{1-6}$ acyl, $R^{1b}$ is H or $C_{1-6}$ alkyl, $R^2$ is $C_{1-12}$ alkyl, $R^{3a}$, $R^{3b}$, $R^{4a}$, and $R^{4b}$ are independently H or $C_{1-6}$ alkyl, each $R^5$ is independently optionally substituted $C_6$-$C_{10}$ aryl, and subscript x is an integer ranging from 1 to 12.

In some embodiments, $R^1$ is —$OR^{1a}$ or —$C(O)OR^{1b}$, and $R^{1b}$ is $C_{1-6}$ alkyl.

A. Preparation of Starting Materials

In some embodiments, the olefin has a structure according to Formula Va:

(Va)

wherein $R^{1a}$ is $C_{1-6}$ acyl (e.g., acetyl). In some embodiments, the olefin is a terminal olefin wherein $R^{3a}$ and $R^{3b}$ are H. In some embodiments, the olefin is an internal olefin wherein at least one of $R^{3a}$ and $R^{3b}$ is an alkyl group. Acylated olefins can be prepared by acylating the corresponding alkenol (e.g., a compound of Formula Va wherein $R^{1a}$, $R^{3a}$, and $R^{3b}$ are H) with an acylating agent. Any acylating agent suitable for forming the acylated olefin according to Formula Va can be used in the methods provided herein. Examples of suitable acylating agents include acid anhydrides (e.g., acetic anhydride), acid chlorides (e.g., acetyl chloride), activated esters (e.g., pentafluorophenyl esters of carboxylic acids), and carboxylic acids used with coupling agents such as dicyclohexylcarbodiimide or carbonyl diimidazole. Typically, 1-10 molar equivalents of the acylating agent with respect to the alkenol will be used. For example, 1-5 molar equivalents of the acylating agent or 1-2 molar equivalents of the acylating agent can be used. In some embodiments, around 1.0, 1.1, 1.2, 1.3, 1.4, or 1.5 molar equivalents of the acylating agent (e.g., acetic anhydride) with respect to the alkenol is used to form the olefin according to Formula Va.

A base can be used to promote acylation of the alkenol by the acylating agent. Examples of suitable bases include potassium carbonate, sodium carbonate, sodium acetate, Huenig's base (i.e., N,N-diisopropylethylamine), lutidines including 2,6-lutidine (i.e., 2,6-dimethylpyridine), triethylamine, tributylamine, pyridine, 2,6-di-tert-butylpyridine, 1,8-diazabicycloundec-7-ene (DBU), quinuclidine, and the collidines. Combinations of two or more bases can be used. Typically, less than one molar equivalent of base with respect to the alkenol will be employed in the methods of the invention. For example, 0.05-0.9 molar equivalents or 0.1-0.5 molar equivalents of the base can be used. In some embodiments, around 0.05, 0.1, 0.15, or 0.2 molar equivalents of the base (e.g., sodium acetate) with respect to the alkenol is used in conjunction with the acylating agent (e.g., acetic anhydride) to form the acylated olefin of Formula Va.

Any suitable solvent can be used for acylating the alkenol. Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof. Alternatively, an alkenol can be combined with an acylating agent such as acetic anhydride and a base such as sodium acetate without an additional solvent. The acylation reaction is typically conducted at temperatures ranging from around 25° C. to about 100° C. for a period of time sufficient to form the acylated olefin of Formula Va. The reaction can be conducted for a period of time ranging from a few minutes to several hours or longer, depending on the particular alkenol and acylating agent used in the reaction. For example, the reaction can be conducted for around 10 minutes, or around 30 minutes, or around 1 hour, or around 2 hours, or around 4 hours, or around 8 hours, or around 12 hours at around 40° C., or around 50° C., or around 60° C., or around 70° C., or around 80° C.

B. Metathesis Catalysts

A number of catalysts can be used for forming metathesis products according to Formula III including, but not limited to, those described in U.S. Pat. No. 9,598,531; WO 00/015399; WO 00/046256; and WO 2013/029079. It has now been discovered that catalysts described below—containing a transition metal and (a) a first carbene ligand, (b) an N-heterocyclic carbene ligand, and (c) a phenylphosphine ligand, a tri(isopropoxy)phosphine ligand, a dimethylsulfoxide ligand, an acetonitrile ligand, or a pyridine ligand—are particularly useful for the industrial-scale preparation of insect pheromones and other compounds having synthetically challenging conjugated diene motifs (e.g., E,Z-1,3-dienes). In some embodiments, the transition metal in the metathesis catalyst is a Group 8 transition metal. The Group 8 transition metal may be, for example, iron, ruthenium, or osmium. In some embodiments, the transition metal is ruthenium. In some embodiments, the catalyst is a ruthenium (II) complex having ligands as described herein. In some embodiments, the catalyst includes (a) a first carbene ligand, (b) an N-heterocyclic carbene ligand, and (c) a phenylphosphine ligand, a tri(isopropoxy)phosphine ligand, or a pyridine ligand.

In some embodiments, the metathesis catalyst has a structure according to Formula VI:

(VI)

wherein:

$R^6$ and $R^7$, together with the carbon atom to which they are attached, form the first carbene ligand;

$R^8$ and $R^9$ are independently anionic ligands;

$L^1$ is the N-heterocyclic carbene ligand; and $L^2$ is the phenylphosphine ligand, the tri(isopropoxy) phosphine ligand, the dimethylsulfoxide ligand, the acetonitrile ligand, or the pyridine ligand.

In some embodiments, the first carbene ligand is optionally substituted alkylidene, optionally substituted benzylidene, optionally substituted indenylidene, optionally substituted vinylidene, or optionally substituted allenylidene. In some embodiments, $R^6$ and $R^7$, together with the carbon atom to which they are attached, form 3-phenyl-1H-inden-1-ylidene, benzylidene, or 3-methylbut-2-en-1-ylidene. In some embodiments, $R^6$ and $R^7$, together with the carbon atom to which they are attached, form 3-phenyl-1H-inden-1-ylidene.

As used herein, the term "phenylphosphine ligand" refers to a phosphine having at least one covalently-bonded phenyl group. In some embodiments, the phenylphosphine ligand is triphenylphosphine, methoxy-diphenyl-phosphine, or phenoxy-diphenyl-phosphine.

In some embodiments, $L^1$ is optionally substituted imidazolidin-2-ylidene. $L^1$ may be, for example, [1,3-bis(2,4,6-trimethylphenyl)-imidazolidin-2-ylidene] or [1,3-bis(2,6-diisopropylphenyl)-imidazolidin-2-ylidene].

In some embodiments, the metathesis catalyst is selected from:

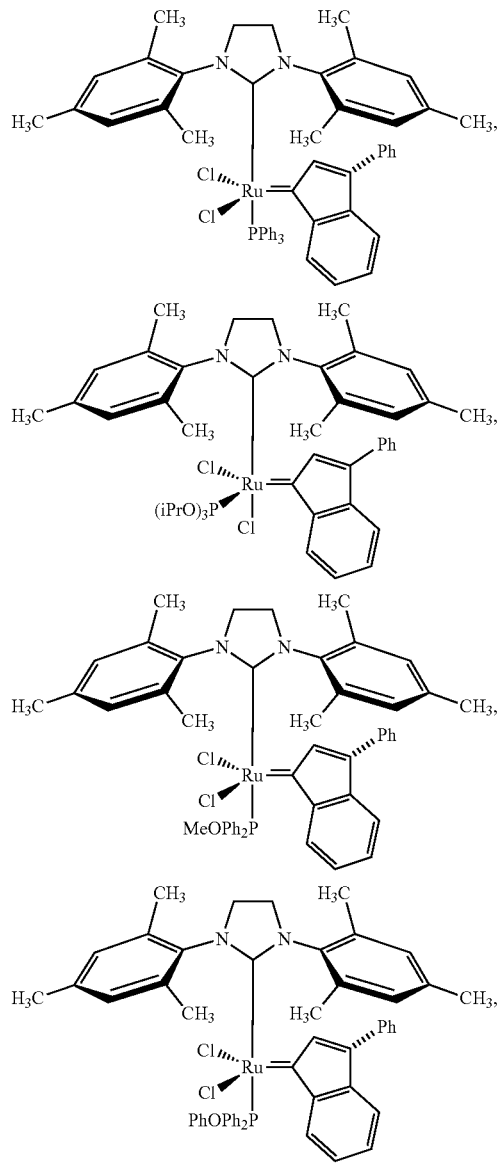

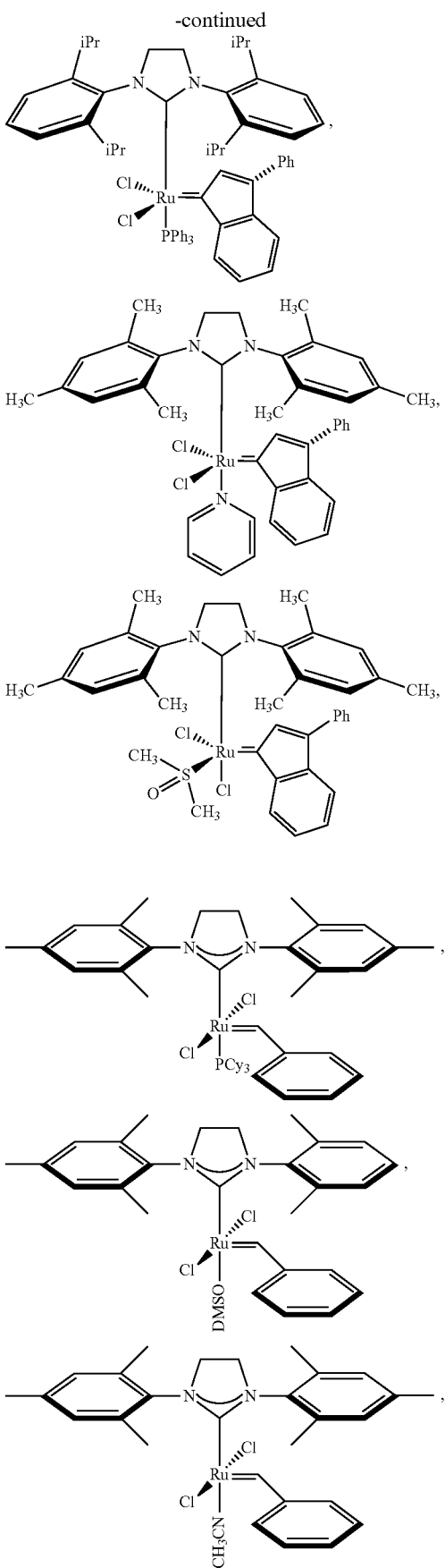

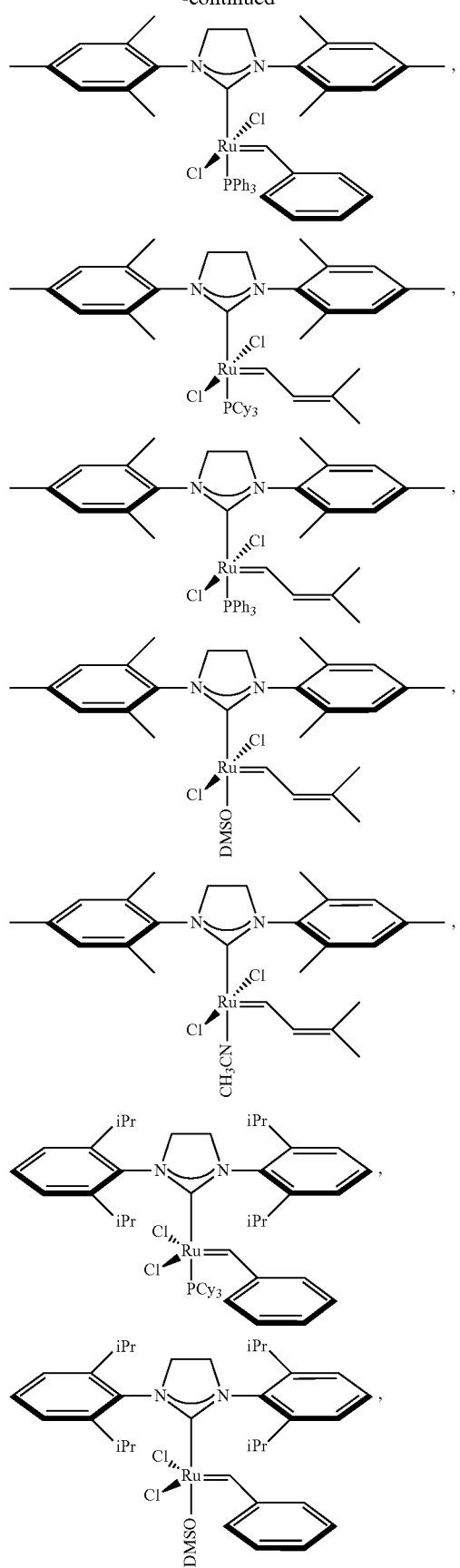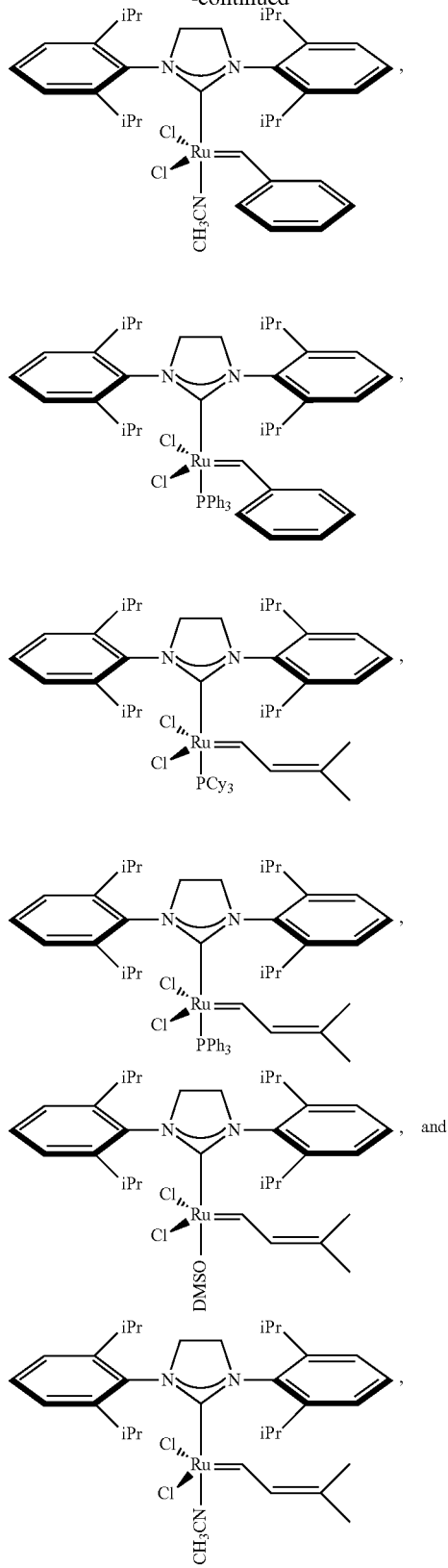
wherein "Ph" represents phenyl, "iPr" represents isopropyl, "Cy" represents cyclohexyl, and DMSO represents dimethylsulfoxide.

C. Metathesis Reaction Conditions

The catalyst is typically provided in the metathesis reaction mixture in a sub-stoichiometric amount (e.g., a catalytic amount). In certain embodiments, that amount is in the range of about 0.001 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 2.5 mol %, less than about 1 mol %, less than about 0.5 mol %, less than about 0.1 mol %, less than about 0.015 mol %, less than about 0.01 mol %, less than about 0.0015 mol %, or less, relative to the limiting reagent. In some embodiments, the catalyst is present in the range of about 2.5 mol % to about 5 mol %, relative to the limiting reagent. In some embodiments, the reaction mixture contains about 0.5 mol % catalyst. In the case where the molecular formula of the catalyst complex includes more than one metal, the amount of the catalyst complex used in the reaction may be adjusted accordingly.

In some embodiments, the amount of the metathesis catalyst in the reaction mixture is less than 0.05 mol % with respect to the total amount of the olefin according to Formula V and the aldehyde according to Formula IV.

In some cases, the metathesis reactions are performed in the absence of solvent (e.g., neat). In some cases, one or more solvents may be used in the metathesis reactions. Examples of solvents that may be suitable for use in the invention include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, as well as mixtures thereof. In some embodiments, the solvent is selected from benzene, toluene, pentane, methylene chloride, and THF. In certain embodiments, the solvent is benzene.

In some embodiments, the metathesis reaction is performed under reduced pressure. This may be advantageous in cases where a volatile byproduct, such as ethylene, may be produced during the course of the metathesis reaction. For example, removal of the ethylene byproduct from the reaction vessel may advantageously shift the equilibrium of the metathesis reaction towards formation of the desired product. In some embodiments, the metathesis reaction is conducted at a pressure of less than about 760 torr. In some embodiments, the metathesis reaction is conducted at a pressure of less than about 600 torr. In some embodiments, the metathesis reaction is conducted at a pressure of less than about 500 torr. In some embodiments, the metathesis reaction is conducted at a pressure of less than about 250 torr. In some embodiments, the metathesis reaction is conducted at a pressure of less than about 100 torr. In some embodiments, the metathesis reaction is conducted at a pressure of less than about 50 torr. In some embodiments, the metathesis reaction is conducted at a pressure of less than about 25 torr. In some embodiments, the metathesis reaction is conducted at a pressure of about 10 torr (e.g., less than 5 torr or less than 1 torr).

Typically, the metathesis reaction is conducted with an excess of the aldehyde according to Formula IV. For example, the aldehyde according to Formula IV and the olefin according to Formula V (e.g., a compound according to Formula Va) can be present in a metathesis reaction mixture in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1.5:1, 1.25:1, or 1.1:1. In some embodiments, the aldehyde according to Formula IV and the olefin according to Formula V are present in a molar ratio of about 5:1. In certain embodiments, the aldehyde according to Formula IV and the olefin according to Formula V are present in a molar ratio of about 2:1.

In some embodiments, the molar ratio of aldehyde according to Formula IV to the olefin according to Formula V ranges from about 1.5:1 to about 3:1.

In some embodiments, the aldehyde according to Formula IV is crotonaldehyde.

Advantageously, the methods of the invention provide metathesis products on a scale ranging from a few milligrams to hundreds of kilograms or more. For example, the metathesis reactions can be conducted using around 1-10 grams of the olefin according to Formula V (e.g., a compound according to Formula Va); or around 10-100 grams of the olefin according to Formula V; or around 100-500 grams of the olefin according to V; or around 500-1000 grams of the olefin according to V. The metathesis reactions can be conducted using at least 1, 5, 10, 25, 50, 100, or 1,000 kilograms of starting material. The metathesis reactions can be conducted using a metathesis reactor as described, for example, in WO 2011/046872, which reactor may be operated in conjunction with one or more downstream separation units for separating and/or recycling particular product or byproduct streams (e.g., an olefin stream, a $C_2$-$C_3$ compound stream, or a $C_3$-$C_5$ compound stream). The metathesis reactor and separation unit(s) can be operated in conjunction with one or more adsorbent beds to facilitate the separation of the metathesized products from the catalyst, as well as washing and drying units for purification of desired products. Metathesis reactions and other steps (e.g., Wittig reactions and acylation reactions) can be conducted to provide products on the scale of metric tons. In some embodiments, the conjugated diene is obtained in an amount ranging from about 100 grams to about 1,000 kilograms.

One of skill in the art will appreciate that the time, temperature and choice of solvent (or absence of solvent) can depend on each other, and that changing one can require changing the others to prepare the metathesis products in the methods of the invention. The metathesis steps can proceed at a variety of temperatures and times. In general, reactions in the methods of the invention are conducted using reaction times of several minutes to several days. For example, reaction times of from about 12 hours to about 7 days can be used. In some embodiments, reaction times of 1-5 days can be used. In some embodiments, reaction times of from about 10 minutes to about 10 hours can be used. In general, reactions in the methods of the invention are conducted at a temperature of from about 0° C. to about 200° C. For example, reactions can be conducted at 15-100° C. In some embodiments, reaction can be conducted at 20-80° C. In some embodiments, reactions can be conducted at 100-150° C.

In certain instances, the efficacy of the metathesis catalyst can be improved (e.g., the turnover number can be increased or the overall catalyst loading may be decreased) through slow addition of the catalyst to a substrate. The overall catalyst loading can be decreased by at least 10%, at least 20%, or at least 30% when administered slowly to achieve the same turnover number as a single, full batch loading. The slow addition of overall catalyst loading can include adding fractional catalyst loadings to the reaction materials at an average rate of approximately 250 ppm by weight of catalyst per hour (ppmwt/hr), 100 ppmwt/hr, 50 ppmwt/hr, 25 ppmwt/hr, 10 ppmwt/hr, 5 ppmwt/hr, 1 ppmwt/hr, 0.5 ppmwt/hr, 0.1 ppmwt/hr, 0.05 ppmwt/hr, or 0.01 ppmwt/hr. In some embodiments, the catalyst is slowly added at a rate of between about 0.01-10 ppmwt/hr, 0.05-5 ppmwt/hr, or 0.1-1 ppmwt/hr. The slow addition of the catalyst can be conducted in batch loadings at frequencies of every 5 minutes, 15 minutes, 30 minutes, 1 hour, 2 hours, 4 hours, 12 hours, or 1 day. In other embodiments, the slow addition is conducted in a continuous addition process.

The metathesis steps can be assessed in terms of the selectivity of the metathesis reaction—that is, the extent to which the reaction produces a particular olefin isomer, whether an E olefin, e.g., a trans olefin according to Formula IIIa:

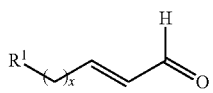

(IIIa)

or a Z olefin, e.g., a cis olefin according to Formula IIIb:

(IIIb)

In general, E-selective catalysts provide metathesis products wherein greater than 50% of the olefin is an E olefin. Preferably, E-selective catalysts provide metathesis products wherein greater than 85% of the olefin is an E olefin. For example, the metathesis product can contain the E olefin in an amount ranging from about 86% to about 100%. The metathesis product can contain the E olefin in an amount ranging from about 86% to about 99%, or from about 88% to about 98%, or from about 90% to about 96%, or from about 92% to about 94%. The metathesis product can contain the E olefin in an amount ranging from about 86% to about 89%, or from about 89% to about 92%, or from about 92% to about 95%, or from about 95% to about 98%. The metathesis product can contain the E olefin in an amount of about 86%, 87%, 88%, 89%, 90%, 91%, 92%, 93%, 94%, 95%, 96%, 97%, 98%, 99%, or 100%.

E-selective catalysts include, but are not limited to, compounds according to Formula VI. E selective-catalysts include, but are not limited to, the catalysts set forth in the following table:

| Structure | Name |
|---|---|
| 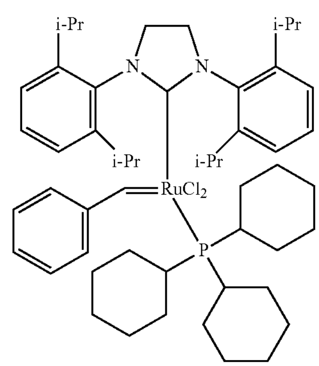 | dichloro[1,3-bis(2,6-isopropylphenyl)-2-imidazolidinylidene](benzylidene)(tricyclohexylphosphine)ruthenium(II) |
| 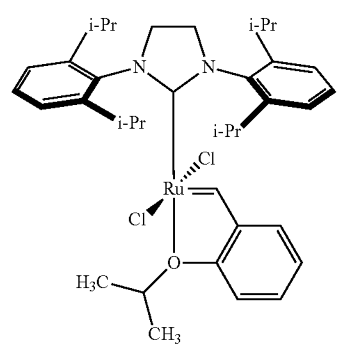 | dichloro[1,3-bis(2,6-isopropylphenyl)-2-imidazolidinylidene](2-isopropoxyphenylmethylene)ruthenium(II) |

| Structure | Name |
|---|---|
| 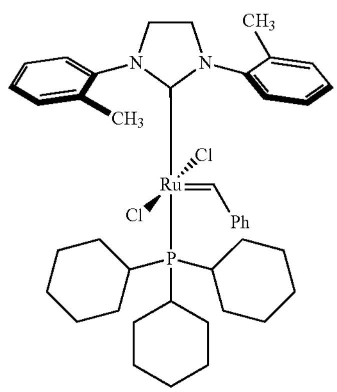 | dichloro[1,3-Bis(2-methylphenyl)-2-imidazolidinylidene](benzylidene)(tricyclohexylphosphine)ruthenium(II) |
| 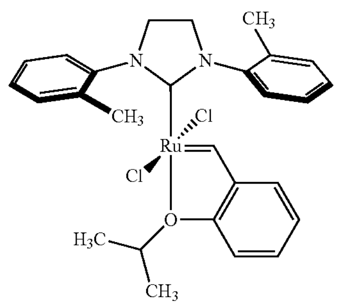 | dichloro[1,3-bis(2-methylphenyl)-2-imidazolidinylidene](2-isopropoxyphenylmethylene)ruthenium(II) |
| 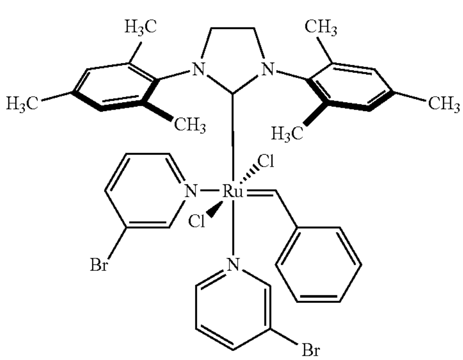 | dichloro[1,3-bis(2,4,6-trimethylphenyl)-2-imidazolidinylidene](benzylidene)bis(3-bromopyridine)ruthenium(II) |
| 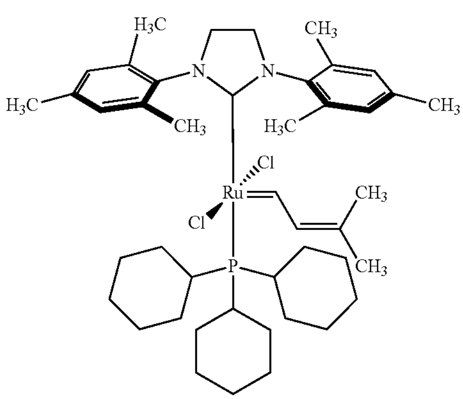 | dichloro[1,3-bis(2,4,6-trimethylphenyl)-2-imidazolidinylidene1(3-methyl-2-butenylidene)(tricyclohexylphosphine)ruthenium(II) |

-continued

| Structure | Name |
|---|---|
| | dichloro[1,3-bis(2,4,6-trimethylphenyl)-2-imidazolidinylidene][3-(2-pyridinyl)propylidene]ruthenium(II) |
| 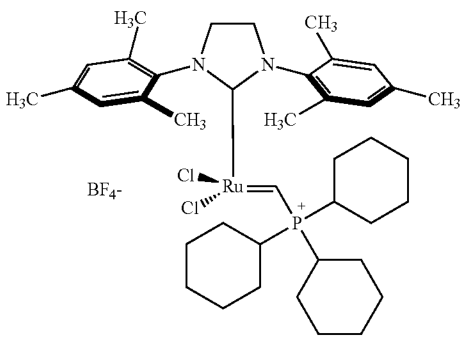 | dichloro[1,3-bis(2,4,6-trimethylphenyl)-2-imidazolidinylidene][(tricyclohexyl-phosphoranyl)methylidene]ruthenium(II) tetrafluoroborate |
| 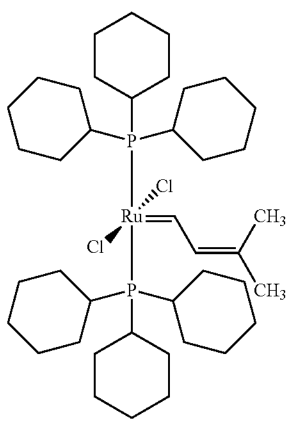 | dichloro(3-methyl-2-butenylidene)bis(tricyclohexylphosphine)ruthenium(II) |
| 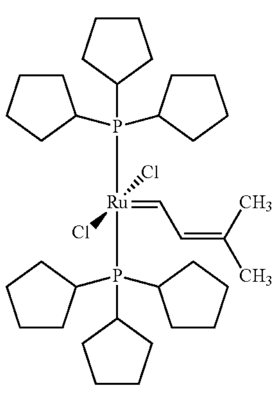 | dichloro(3-methyl-2-butenylidene)bis(tricyclopentylphosphine)ruthenium(II) |

-continued

| Structure | Name |
|---|---|
| 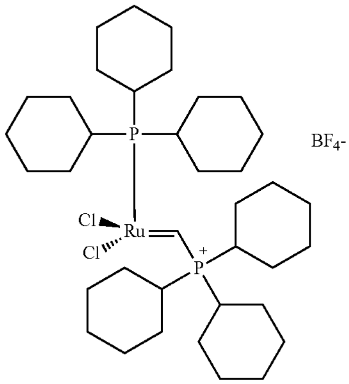 | dichloro(tricyclohexylphosphine)[(tricyclohexylphosphoranyl)methylidenel]ruthenium(II) tetrafluoroborate |
| 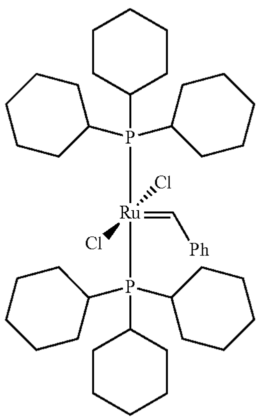 | bis(tricyclohexylphosphine) benzylidine ruthenium(IV) dichloride |
| 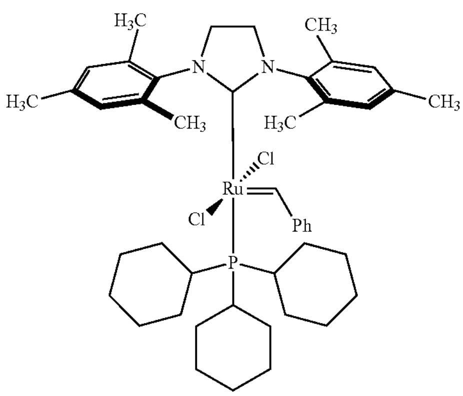 | [1,3-bis-(2,4,6-trimethylphenyl)-2-imidazolidinylidene]dichloro(phenylmethylene)(tricyclohexylphosphine)ruthenium |
| 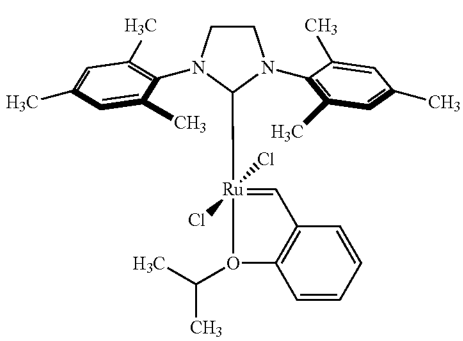 | (1,3-bis-(2,4,6-trimethylphenyl)-2-imidazolidinylidene)dichloro(o-isopropoxyphenylmethylene)ruthenium |

| Structure | Name |
|---|---|
| 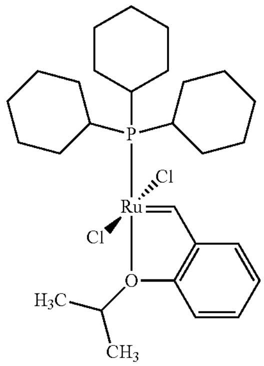 | dichloro(o-isopropoxyphenylmethylene)(tricyclohexylphosphine)ruthenium(II) |

In general, Z-selective catalysts provide metathesis products wherein greater than 15% of the olefin is a Z olefin. For example, the metathesis product can contain the Z olefin in an amount ranging from about 20% to about 100%. The metathesis product can contain the Z olefin in an amount ranging from about 25% to about 95%, or from about 30% to about 90%, or from about 35% to about 85%, or from about 40% to about 80%, or from about 45% to about 75%, or from about 50% to about 70%, or from about 55% to about 65%. The metathesis product can contain the Z olefin in an amount ranging from about 15% to about 20%, or from about 20% to about 25%, or from about 25% to about 30%, or from about 30% to about 35%, or from about 35% to about 40%, or from about 40% to about 45%, or from about 45% to about 50%, or from about 50% to about 60%, or from about 60% to about 65%, or from about 65% to about 70%, or from about 70% to about 75%, or from about 75% to about 80%, or from about 80% to about 85%, or from about 85% to about 90%, or from about 90% to about 95%, or from about 95% to about 99%. The metathesis product can contain the Z olefin in an amount of about 55%, 60%, 65%, 70%, 75%, 80%, 85%, 86%, 87%, 88%, 89%, 90%, 91%, 92%, 93%, 94%, 95%, 96%, 97%, 98%, 99%, or 100%.

Z-selective catalysts are described, for example, in WO 2017/087710 and WO 2018/150379, as well as by Shahane et al. (Shahane, S., et al. *ChemCatChem*, 2013. 5(12): p. 3436-3459), which are incorporated herein by reference in their entirety. Specific catalysts 1-5, shown below, have been described previously (Khan, R. K., et al. *J. Am. Chem. Soc.*, 2013. 135(28): p. 10258-61; Hartung, J. et al. *J. Am. Chem. Soc.*, 2013. 135(28): p. 10183-5; Rosebrugh, L. E., et al. *J. Am. Chem. Soc.*, 2013. 135(4): p. 1276-9; Marx, V. M., et al. *J. Am. Chem. Soc.*, 2013. 135(1): p. 94-7; Herbert, M. B., et al. *Angew. Chem. Int. Ed. Engl.*, 2013. 52(1): p. 310-4; Keitz, B. K., et al. *J. Am. Chem. Soc.*, 2012. 134(4): p. 2040-3; Keitz, B. K., et al. *J. Am. Chem. Soc.*, 2012. 134(1): p. 693-9; Endo, K. et al. *J. Am. Chem. Soc.*, 2011. 133(22): p. 8525-7).

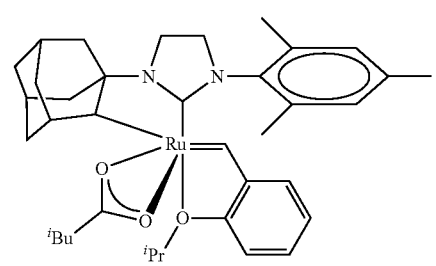

1

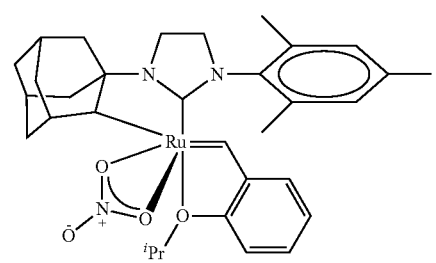

2

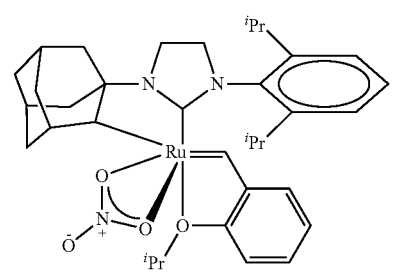

3

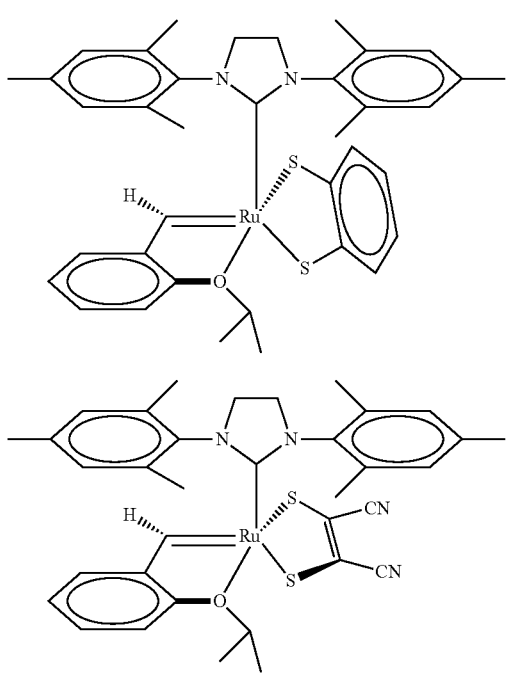

Additional Z-selective catalysts are described in (Cannon and Grubbs 2013; Bronner et al. 2014; Hartung et al. 2014; Pribisko et al. 2014; Quigley and Grubbs 2014) and are herein incorporated by reference in their entirety. Such metathesis catalysts include, but are not limited to, neutral ruthenium or osmium metal carbene complexes that possess metal centers that are formally in the +2 oxidation state, have an electron count of 16, are penta-coordinated, and are of the general formula LL'AA'M=CRbRc or LL'AA'M=(C=)nCRbRc (Pederson and Grubbs 2002); wherein M is ruthenium or osmium;

L and L' are each independently any neutral electron donor ligand and preferably selected from phosphine, sulfonated phosphine, phosphite, phosphinite, phosphonite, arsine, stibnite, ether, amine, amide, imine, sulfoxide, carboxyl, nitrosyl, pyridine, thioether, or heterocyclic carbenes; and A and A' are anionic ligands independently selected from halogen, hydrogen, $C_1$-$C_{20}$ alkyl, aryl, $C_1$-$C_{20}$ alkoxide, aryloxide, $C_2$-$C_{20}$ alkoxycarbonyl, arylcarboxylate, $C_1$-$C_{20}$ carboxylate, arylsulfonyl, $C_1$-$C_{20}$ alkylsulfonyl, $C_1$-$C_{20}$ alkylsulfinyl; each ligand optionally being substituted with $C_1$-$C_5$ alkyl, halogen, $C_1$-$C_5$ alkoxy; or with a phenyl group that is optionally substituted with halogen, $C_1$-$C_5$ alkyl, or $C_1$-$C_5$ alkoxy; and A and A' together may optionally comprise a bidentate ligand; and $R_b$ and $R_c$ are independently selected from hydrogen, $C_1$-$C_{20}$ alkyl, aryl, $C_1$-$C_{20}$ carboxylate, $C_1$-$C_{20}$ alkoxy, aryloxy, $C_1$-$C_{20}$ alkoxycarbonyl, $C_1$-$C_{20}$ alkylthio, $C_1$-$C_{20}$ alkylsulfonyl and $C_1$-$C_{20}$ alkylsulfinyl, each of $R_b$ and $R_c$ optionally substituted with $C_1$-$C_5$ alkyl, halogen, $C_1$-$C_5$ alkoxy or with a phenyl group that is optionally substituted with halogen, $C_1$-$C_5$ alkyl, or $C_1$-$C_5$ alkoxy.

D. Wittig Reaction Conditions

Metathesis products can be converted to conjugated dienes via Wittig reaction with ylides, including ylides generated from alkylphosphonium halides according to Formula IIa:

$$(R^5)_3 \overset{\oplus}{P} \diagup \diagdown R^2 \cdot \quad \overset{\ominus}{X} \tag{IIa}$$

Typically, 1-5 molar equivalents (e.g., 1-2 molar equivalents) of the alkylphosphonium halide with respect to the metathesis product intermediate will be employed in the Wittig reaction. In some embodiments, around 1.0, 1.1, 1.2, 1.3, 1.4, or 1.5 molar equivalents of the alkylphosphonium halide (e.g., ethyltriphenylphosphonium bromide) with respect to the metathesis product intermediate is employed for forming the conjugated diene. Prior to addition of the metathesis product, the alkylphosphonium halide may be treated with a base to form the corresponding phosphonium ylide. Suitable bases for forming phosphonium ylides include, but are not limited to, sodium tert-butoxide, potassium tert-butoxide, sodium methoxide, sodium hydride, triethylamine, lithium diisopropylamide, and the like. Typically, equimolar amounts of the base and the alkylphosphonium halide will be employed for generating the ylide to be used in the Wittig reaction. Suitable solvents for generating the ylide include, but are not limited to, toluene, tetrahydrofuran, diethyl ether, mixtures thereof. Reaction of the resulting ylide with the metathesis product according to Formula III is typically conducted at temperatures ranging from around 0° C. to about 30° C. for a period of time sufficient to form the conjugated diene according to Formula I. The reaction can be conducted for a period of time ranging from a few minutes to several hours or longer, depending on the particular ylide and metathesis produce used in the reaction. For example, the reaction can be conducted for around 10 minutes, or around 30 minutes, or around 1 hour, or around 2 hours, or around 4 hours, or around 8 hours, or around 12 hours at around 0° C., or around 2-4° C., or up to 20-25° C.

In some embodiments, the metathesis product according to Formula III of step (ii) is used in crude form (e.g., partially purified, or unpurified) in the Wittig reaction in step (iii). In some such embodiments, the first reaction mixture (a metathesis reaction mixture) may be combined with the ylide in a second reaction mixture (a Wittig reaction mixture). In some embodiments, the base in step (iii) is potassium tert-butoxide or sodium tert-butoxide.

Depending on factors such as the structure of the aldehyde metathesis product (e.g., a compound of Formula III) and the phosphonium ylide (e.g., a compound of Formula II), the Wittig reaction may provide the olefin product (e.g., the olefin adjacent to $R^2$ in a conjugated diene of Formula I) in a Z-selective manner or an E-selective manner. For example, the Wittig product can contain a Z olefin or an E olefin in an amount ranging from about 20% to about 100%. The Wittig product can contain the Z olefin or E olefin in an amount ranging from about 25% to about 95%, or from about 30% to about 90%, or from about 35% to about 85%, or from about 40% to about 80%, or from about 45% to about 75%, or from about 50% to about 70%, or from about 55% to about 65%. The Wittig product can contain the Z olefin or E olefin in an amount ranging from about 15% to about 20%, or from about 20% to about 25%, or from about 25% to about 30%, or from about 30% to about 35%, or from about 35% to about 40%, or from about 40% to about 45%, or from about 45% to about 50%, or from about 50% to about 60%, or from about 60% to about 65%, or from about 65% to about 70%, or from about 70% to about 75%, or from about 75% to about 80%, or from about 80% to about 85%, or from about 85% to about 90%, or from about 90% to about 95%, or from about 95% to about 99%. The Wittig product can contain the Z olefin or E olefin in an amount of about 55%, 60%, 65%, 70%, 75%, 80%, 85%, 86%, 87%, 88%, 89%, 90%, 91%, 92%, 93%, 94%, 95%, 96%, 97%, 98%, 99%, or 100%.

In some embodiments, excess lithium salts (e.g., a lithium halide such as lithium chloride) may be included in the Wittig reaction mixture to promote formation of an E-alkene (e.g., an E-olefin adjacent to $R^2$ in conjugated dienes according to Formula I, Formula Ib, or Formula Ic). See, e.g., Schlosser et al. *Angew. Chem. Int. Ed. Eng.* 1966, 5, 126; Hodgson, et al. *J. Am. Chem. Soc.,* 2008, 130, 16500-16501; and He, et al. *Synlett* 2018, 29, 1117-1121.

In some embodiments, the molar ratio of E olefin to Z olefin formed during step (ii) is greater than 20:1. In some embodiments, the molar ratio of Z olefin to E olefin formed during step (iii) is greater than 8:1.

Various conjugated dienes, including insect pheromones and related compounds, can be prepared according to the methods provided herein. In some embodiments, the conjugated diene is an E,Z-diene according to Formula Ia:

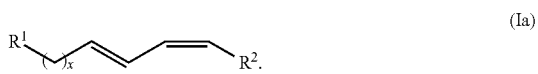

In some embodiments, the conjugated diene is an E,E-diene according to Formula Ib:

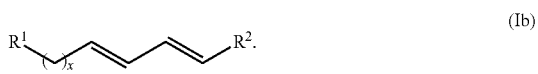

In some embodiments, the conjugated diene is a Z,E-diene according to Formula Ic:

In some embodiments, the conjugated diene is a Z,Z-diene according to Formula Id:

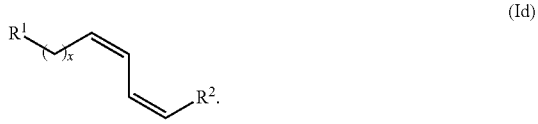

The conjugated diene according to Formula I can be, for example, (4E,6Z)-hexadeca-4,6-dien-1-ol; (4E,6Z)-hexadeca-4,6-dien-1-yl acetate; (4E,6Z)-hexadeca-4,6-dienal; (2E,4Z)-deca-2,4-dienal; (9E,11Z)-hexadeca-9,11-dien-1-yl acetate; (9E,11Z)-hexadeca-9,11-dienal; (10E,12Z)-hexadeca-10,12-dien-1-ol; (10E,12Z)-hexadeca-10,12-dien-1-yl acetate; (10E,12Z)-hexadeca-10,12-dienal; (3E,5Z)-tetradeca-3,5-dien-1-yl acetate; (11E,13Z)-hexadeca-11,13-dien-1-ol; (11E,13Z)-hexadeca-11,13-dien-1-yl acetate; (11E,13Z)-hexadeca-11,13-dienal; (8E,10Z)-tetradeca-8,10-dien-1-yl acetate; (8E,10Z)-tetradeca-8,10-dienal; (9E,11Z)-tetradeca-9,11-dien-1-yl acetate; (3E,5Z)-dodeca-3,5-dien-1-yl acetate; (5E,7Z)-dodeca-5,7-dien-1-ol; (5E,7Z)-dodeca-5,7-dien-1-yl acetate; (5E,7Z)-dodeca-5,7-dienal; (10E,12Z)-tetradeca-10,12-dien-1-yl acetate; (7E,9Z)-dodeca-7,9-dien-1-ol; (7E,9Z)-dodeca-7,9-dien-1-yl acetate; (7E,9Z)-dodeca-7,9-dienal; (8E,10Z)-dodeca-8,10-dien-1-ol; (8E,10Z)-dodeca-8,10-dien-1-yl acetate; (8E,10Z)-dodeca-8,10-dienal; (8E,10Z)-pentadeca-8,10-dien-1-ol; (8E,10Z)-pentadeca-8,10-dien-1-yl acetate; or (9E,11Z)-pentadeca-9,11-dienal.

In some embodiments, the conjugated diene is selected from (7E,9Z)-dodeca-7,9-dien-1-yl acetate, (3E,5Z)-dodeca-3,5-dien-1-yl acetate, (3E,5Z)-dodeca-3,5-dien-1-yl acetate, (5E,7Z)-dodeca-5,7-dien-1-yl acetate, (8E,10Z)-dodeca-8,10-dien-1-yl acetate, (5E,7Z)-dodeca-5,7-dien-1-ol, (5E,7Z)-dodeca-5,7-dienal, (7E,9Z)-dodeca-7,9-dien-1-ol, (7E,9Z)-dodeca-7,9-dienal, (8E,10Z)-dodeca-8,10-dien-1-ol, (8E,10Z)-dodeca-8,10-dienal, (2E,4Z)-hepta-2,4-dien-1-ol, (2E,4Z)-hepta-2,4-dienal, (2E,4Z)-octa-2,4-dienal, (4E,6Z)-octa-4,6-dienoic acid, (2E,4Z)-deca-2,4-dienal, ethyl (2E,4Z)-deca-2,4-dienoate, (10E,12Z)-tetradeca-10,12-dien-1-yl acetate, (3E,5Z)-tetradeca-3,5-dienoic acid, (3E,5Z)-tetradeca-3,5-dien-1-yl acetate, (8E,10Z)-tetradeca-8,10-dienal, (8E,10Z)-tetradeca-8,10-dien-1-yl acetate, (9E,11Z)-tetradeca-9,11-dien-1-yl acetate, (6E,8Z)-pentadeca-6,8-dienal, (8E,10Z)-pentadeca-8,10-dien-1-ol, (8E,10Z)-pentadeca-8,10-dien-1-yl acetate, (9E,11Z)-pentadeca-9,11-dienal, (10E,12Z)-hexadeca-10,12-dien-1-ol, (10E,12Z)-hexadeca-10,12-dienal, (10E,12Z)-hexadeca-10,12-dien-1-yl acetate, (11E,13Z)-hexadeca-11,13-dien-1-ol, (11E,13Z)-hexadeca-11,13-dienal, (11E,13Z)-hexadeca-11,13-dien-1-yl acetate, (9E,11Z)-hexadeca-9,11-dienal, and (9E,11Z)-hexadeca-9,11-dien-1-yl acetate. In some embodiments, the conjugated diene is (7E,9Z)-dodeca-7,9-dien-1-yl acetate.

III. Examples

Example 1. Synthesis of Oct-7-en-1-yl Acetate (7-OAc)

Under an inert atmosphere, a vessel is charged with oct-7-en-1-ol (1 mol eq.) and a catalytic amount of anhydrous sodium acetate (0.1 mol eq.). The suspension was agitated and heated to ~55° C. Acetic anhydride (1.2 mol eq.) was added to the mixture at a rate such that the reaction temperature did not exceed 60° C., approximately 1 hour. The mixture was agitated at ~60° C. for an additional hour and then allowed to cool to ambient temperature. The crude mixture was washed once with one reaction volume of deionized (DI) water, twice with one reaction volume of a saturated sodium carbonate solution, and finally twice with one reaction volume of DI water. The crude mixture was then dried via azeotropic distillation with toluene at ~45° C. and 15 Torr to obtain a pale yellow oil. The oil was then purified by vacuum distillation to yield the final product in ~85-90% molar yield and overall purity of ~93%. The major contaminant was E/Z-oct-6-en-1-yl acetate which was derived from E/Z-oct-6-en-1-ol present in the oct-7-en-1-ol feedstock. The reaction was also performed on a scale of approximately 700 g of oct-7-en-1-ol, resulting in molar yields ranging from 95% to 98%.

Example 2. Synthesis of E-9-Oxonon-7-en-1-yl Acetate Via Cross-metathesis of 7-OAc and Crotonaldehyde Under an inert atmosphere, a vessel was charged with 7-OAc (200 g, 1 mol eq.) and freshly distilled crotonaldehyde (2 mol eq.). With agitation an inert gas was introduced via a cannula below the surface of the feedstock with the outlet being directed first through a −10° C. condenser and finally through a silicone oil bubbler. Metathesis catalyst 1,3-bis(2,4,6-trimethylphenyl)-2-imidazolidinylideneldichloro(3-phenyl-1H-inden-1-ylidene)(triphenylphosphine) ruthenium (II) (0.015 mol % relative to all feedstocks) was added as a solution in toluene. Propylene gas evolution was observed immediately and slowly subsided over the next two hours. Reaction progress was monitored by GC-FID analysis of reaction mixture aliquots. The conversion of 7-OAc in all products was determined to be >80% molar, the E-selectivity at the 7-position >97% and the selectivity for the conjugated aldehyde >85% over other metathesis co-products. Excess crotonaldehyde was stripped under vacuum, and the crude mixture was carried directly into the next synthetic step without isolation. The reaction was also performed on a scale of approximately 700 g of oct-7-en-1-yl acetate, resulting in molar yields ranging from 95% to 98%.

Example 3. Synthesis of E,Z-Dodeca-7,9-dien-1-yl Acetate (E7Z9-12Ac) Via Wittig Reaction Under an inert atmosphere, a vessel was charged with propyltriphenylphosphonium bromide (1.2 mol eq.) and THF to a make a 0.7M-1 M solution. The mixture was agitated and solid sodium tert-butoxide (1.2 mol eq.) was added portion-wise over the course of 30 min to yield a bright orange solution with a precipitate. The reaction mixture was then cooled in an ice bath to 2-4° C. and crude E-9-oxonon-7-en-1-yl acetate product (1 mol eq.) from Example 2, including all other remaining components, was added dropwise either neat or as a solution in THF over the course of 60 minutes. The mixture was stirred at 0° C. through the course of the reaction. After 2 hours, GC-FID analysis of indicated that the conjugated aldehyde intermediate was fully consumed. THF was then removed in vacuo and an equal volume of hexanes was added. The crude mixture was cooled to 4° C. and the inorganic salts were allowed to precipitate over the next 24 hours. The supernatant was decanted and the hexanes were removed in vacuo. The residue was fractionally distilled at 10 Torr using a short-path apparatus to provide E,Z-dodeca-7,9-dien-1-yl acetate with >90% purity, >87% isomeric purity, and >75% yield (including distillation losses). The reaction was also performed on a scale of approximately 100 g, resulting in molar yields ranging from 65% to 75%.

IV. Exemplary Embodiments

Exemplary embodiments provided in accordance with the presently disclosed subject matter include, but are not limited to, the claims and the following embodiments:

1. A method for preparing a conjugated diene according to Formula I:

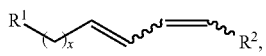

(I)

the method comprising:
(i) forming a reaction mixture comprising:
an olefin according to Formula V:

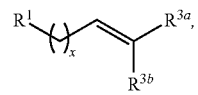

(V)

an aldehyde according to Formula IV:

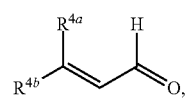

(IV)

and
a metathesis catalyst comprising a transition metal and (a) a first carbene ligand, (b) an N-heterocyclic carbene ligand, and (c) a phenylphosphine ligand, a tri(isopropoxy)phosphine ligand, a dimethylsulfoxide ligand, an acetonitrile ligand, or a pyridine ligand;
(ii) maintaining the reaction mixture under conditions sufficient to form a metathesis product according to Formula III:

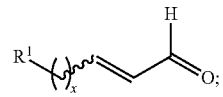

(III)

and
(iii) combining the metathesis product according to Formula III with a phosphonium ylide according to Formula II:

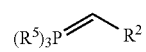

(II)

under conditions sufficient to form the conjugated diene according to Formula I, wherein:
$R^1$ is —$OR^{1a}$, —$C(O)OR^{1b}$, or —$C(O)H$,
$R^{1a}$ is H or $C_{1-6}$ acyl,
$R^{1b}$ is H or $C_{1-6}$ alkyl,
$R^2$ is $C_{1-12}$ alkyl,
$R^{3a}$, $R^{3b}$, $R^{4a}$, and $R^{4b}$ are independently H or $C_{1-6}$ alkyl,
each $R^5$ is independently optionally substituted $C_6$-$C_{10}$ aryl, and
subscript x is an integer ranging from 1 to 12.

2. The method of embodiment 1, wherein the metathesis catalyst has a structure according to Formula VI:

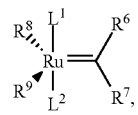

(VI)

wherein:

R[6] and R[7], together with the carbon atom to which they are attached, form the first carbene ligand;

R[8] and R[9] are independently anionic ligands;

L[1] is the N-heterocyclic carbene ligand; and

L[2] is the phenylphosphine ligand, the tri(isopropoxy) phosphine ligand, the dimethylsulfoxide ligand, the acetonitrile ligand, or the pyridine ligand.

3. The method of embodiment 1 or embodiment 2, wherein the first carbene ligand is optionally substituted alkylidene, optionally substituted benzylidene, optionally substituted indenylidene, optionally substituted vinylidene, or optionally substituted allenylidene.

4. The method of embodiment 2 or embodiment 3, wherein R[6] and R[7], together with the carbon atom to which they are attached, form 3-phenyl-1H-inden-1-ylidene, benzylidene, or 3-methylbut-2-en-1-ylidene.

5. The method of embodiment 4, wherein R[6] and R[7], together with the carbon atom to which they are attached, form 3-phenyl-1H-inden-1-ylidene.

6. The method of any one of embodiments 1-5, wherein L[1] is optionally substituted imidazolidin-2-ylidene.

7. The method of any one of embodiments 1-6, wherein the metathesis catalyst is selected from:

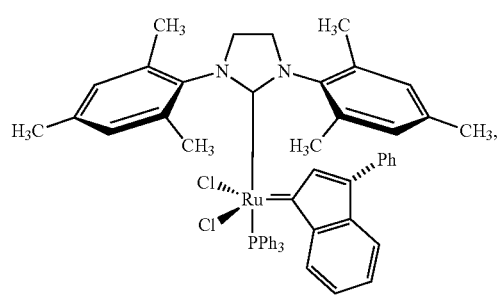

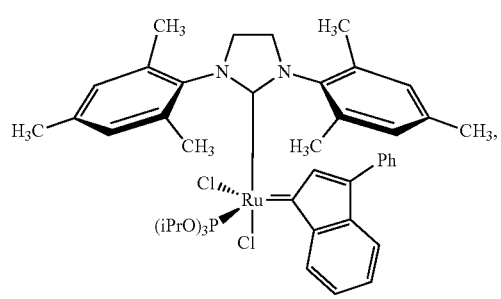

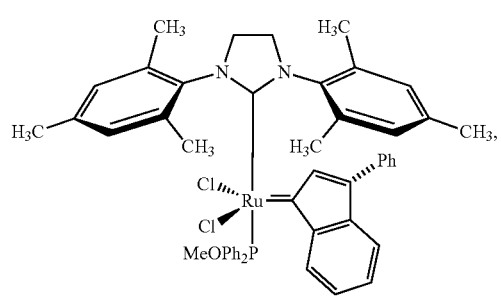

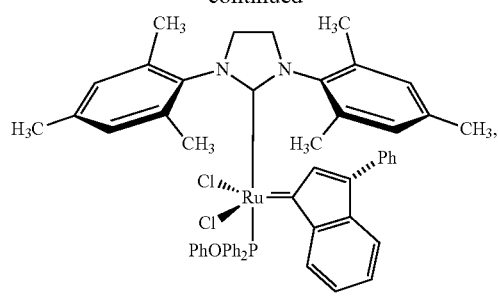

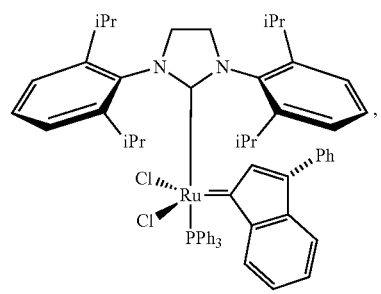

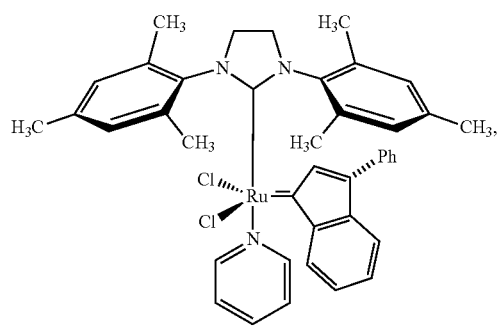

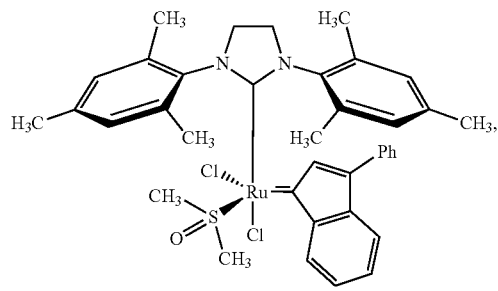

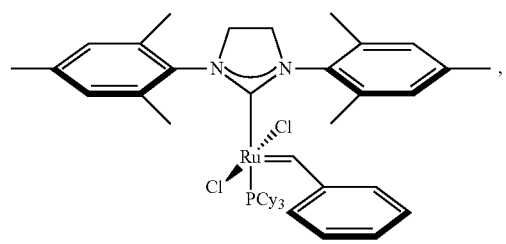

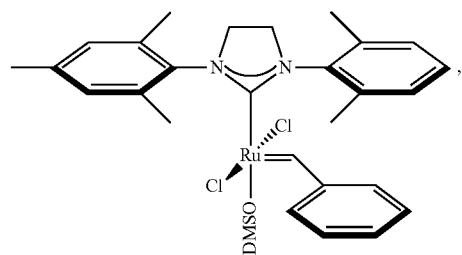

-continued
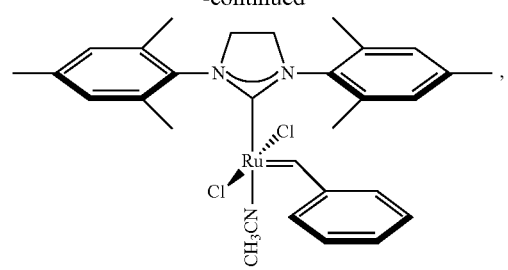
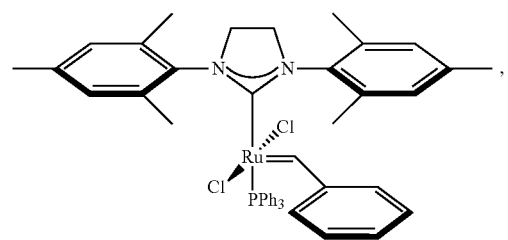
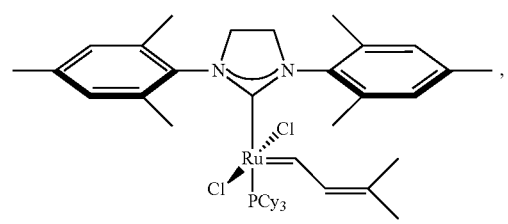
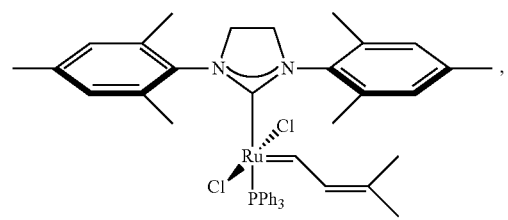
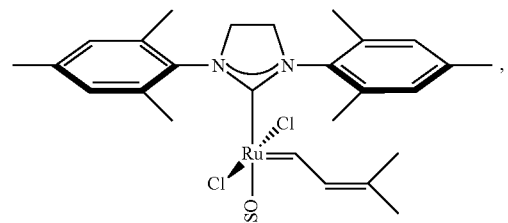
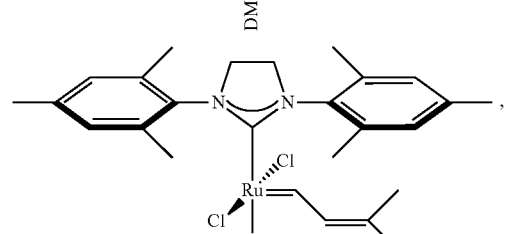
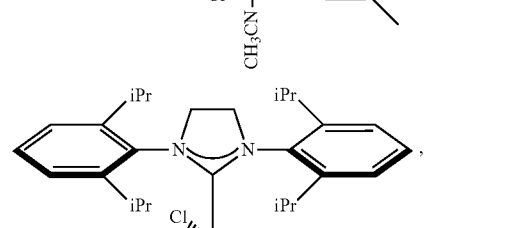
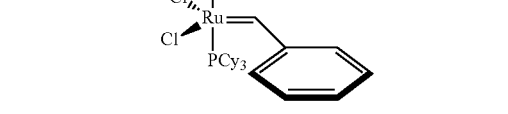
-continued
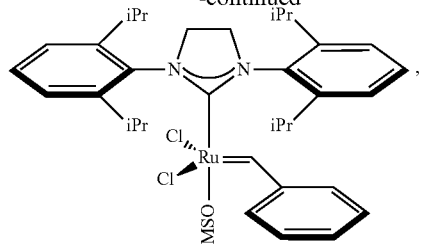
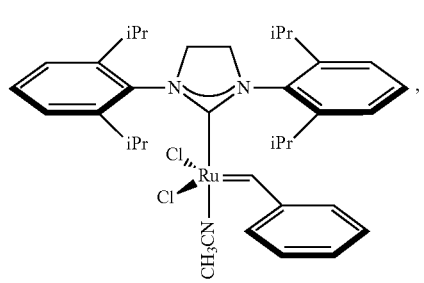
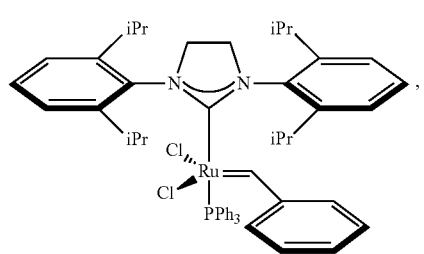
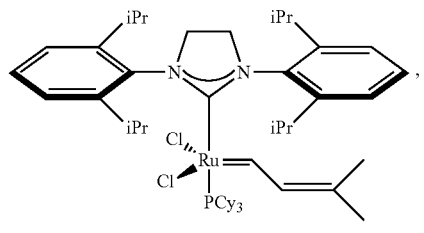
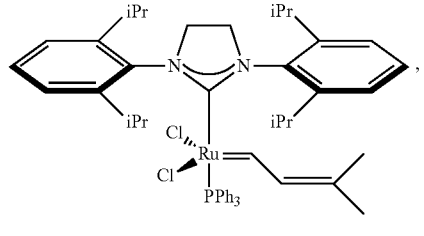
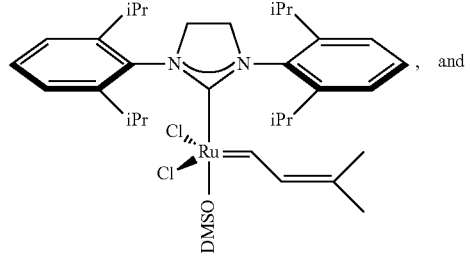, and

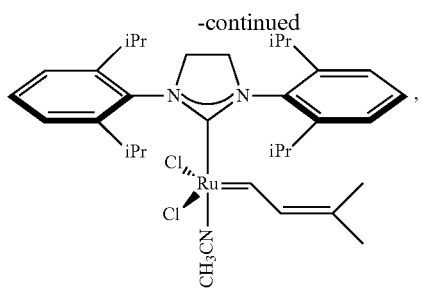

wherein "Ph" represents phenyl, "iPr" represents isopropyl, "Cy" represents cyclohexyl, and DMSO represents dimethylsulfoxide.

8. The method of any one of embodiments 1-7, wherein the amount of the metathesis catalyst in the reaction mixture is less than 0.05 mol % with respect to the total amount of the olefin according to Formula V and the aldehyde according to Formula IV.
9. The method of any one of embodiments 1-8, wherein the molar ratio of the aldehyde according to Formula IV to the olefin according to Formula V ranges from about 1.5:1 to about 3:1.
10. The method of any one of embodiments 1-9, wherein the aldehyde according to Formula IV is crotonaldehyde.
11. The method of any one of embodiments 1-10, wherein the metathesis product according to Formula III of step (ii) is not purified prior to step (iii).
12. The method of any one of embodiments 1-11, wherein the phosphonium ylide according to Formula II is formed by reacting a base with an alkylphosphonium halide according to Formula IIIa

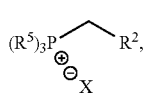

(IIa)

wherein X is halogen.
13. The method of embodiment 12, wherein the base is sodium tert-butoxide.
14. The method of any one of embodiments 1-13, wherein the conjugated diene is selected from an E,Z-diene, an E,E-diene, a Z,E-diene, a Z,Z-diene, and combinations thereof.
15. The method of any one of embodiments 1-14, wherein the conjugated diene is selected from the group consisting of (7E,9Z)-dodeca-7,9-dien-1-yl acetate, (3E,5Z)-dodeca-3,5-dien-1-yl acetate, (3E,5Z)-dodeca-3,5-dien-1-yl acetate, (5E,7Z)-dodeca-5,7-dien-1-yl acetate, (8E,10Z)-dodeca-8,10-dien-1-yl acetate, (5E,7Z)-dodeca-5,7-dien-1-ol, (5E,7Z)-dodeca-5,7-dienal, (7E,9Z)-dodeca-7,9-dien-1-ol, (7E,9Z)-dodeca-7,9-dienal, (8E,10Z)-dodeca-8,10-dien-1-ol, (8E,10Z)-dodeca-8,10-dienal, (2E,4Z)-hepta-2,4-dien-1-ol, (2E,4Z)-hepta-2,4-dienal, (2E,4Z)-octa-2,4-dienal, (4E,6Z)-octa-4,6-dienoic acid, (2E,4Z)-deca-2,4-dienal, ethyl (2E,4Z)-deca-2,4-dienoate, (10E,12Z)-tetradeca-10,12-dien-1-yl acetate, (3E,5Z)-tetradeca-3,5-dienoic acid, (3E,5Z)-tetradeca-3,5-dien-1-yl acetate, (8E,10Z)-tetradeca-8,10-dienal, (8E,10Z)-tetradeca-8,10-dien-1-yl acetate, (9E,11Z)-tetradeca-9,11-dien-1-yl acetate, (6E,8Z)-pentadeca-6,8-dienal, (8E,10Z)-pentadeca-8,10-dien-1-ol, (8E,10Z)-pentadeca-8,10-dien-1-yl acetate, (9E,11Z)-pentadeca-9,11-dienal, (10E,12Z)-hexadeca-10,12-dien-1-ol, (10E,12Z)-hexadeca-10,12-dienal, (10E,12Z)-hexadeca-10,12-dien-1-yl acetate, (11E,13Z)-hexadeca-11,13-dien-1-ol, (11E,13Z)-hexadeca-11,13-dienal, (11E,13Z)-hexadeca-11,13-dien-1-yl acetate, (9E,11Z)-hexadeca-9,11-dienal, and (9E,11Z)-hexadeca-9,11-dien-1-yl acetate.

16. The method of any one of embodiments 1-15, wherein the conjugated diene is (7E,9Z)-dodeca-7,9-dien-1-yl acetate.
17. The method of any one of embodiments 1-16, wherein the molar ratio of E olefin to Z olefin formed during step (ii) is greater than 20:1.
18. The method of any one of embodiments 1-17, wherein the molar ratio of Z olefin to E olefin formed during step (iii) is greater than 8:1.
19. The method of any one of embodiments 1-18, wherein:

the olefin according to Formula V is oct-7-en-1-yl acetate,
the aldehyde according to Formula IV is crotonaldehyde,
the metathesis product according to Formula III is E-9-oxonon-7-en-1-yl acetate,
the phosphonium ylide according to Formula II is triphenyl(propylidene)$\lambda^5$-phosphane, and
the conjugated diene is E,Z-dodeca-7,9-dien-1-yl acetate.

20. The method of embodiment 19, wherein the metathesis catalyst is 1,3-bis(2,4,6-trimethylphenyl)-2-imidazolidinylideneldichloro(3-phenyl-1H-inden-1-ylidene)(triphenylphosphine)ruthenium (II):

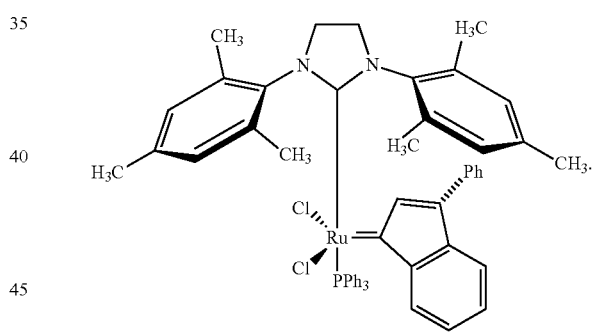

Although the foregoing has been described in some detail by way of illustration and example for purposes of clarity and understanding, one of skill in the art will appreciate that certain changes and modifications can be practiced within the scope of the appended claims. All publications, patents, patent applications, and sequence accession numbers cited herein are hereby incorporated by reference in their entirety for all purposes.

What is claimed is:

1. A method for preparing a conjugated diene according to Formula I:

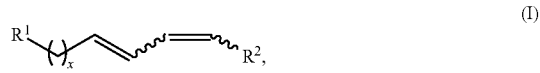

(I)

the method comprising:
(i) forming a reaction mixture comprising:
an olefin according to Formula V:

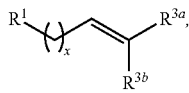  (V)

a crotonaldehyde, and
a metathesis catalyst according to Formula VI:

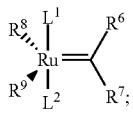  (VI)

(ii) maintaining the reaction mixture under conditions sufficient to form a metathesis product according to Formula III:

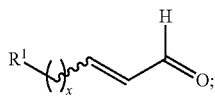  (III)

and
(iii) combining the metathesis product according to Formula III with a phosphonium ylide according to Formula II:

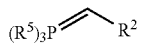  (II)

under conditions sufficient to form the conjugated diene according to Formula I, wherein:
$R^1$ is $-OR^{1a}$, $-C(O)OR^{1b}$, or $-C(O)H$,
$R^{1a}$ is $C_{1-6}$ acyl or H,
$R^{1b}$ is H or $C_{1-6}$ alkyl,
$R^2$ is $C_{3-12}$ alkyl or $C_{1-2}$ alkyl,
$R^{3a}$ and $R^{3b}$ are independently H or $C_{1-6}$ alkyl,
each $R^5$ is independently optionally substituted $C_6$-$C_{10}$ aryl,
subscript x is an integer ranging from 6 to 12 or an integer ranging from 1 to 5,
$R^6$ and $R^7$, together with the carbon atom to which they are attached, form a first carbene ligand,
$R^8$ and $R^9$ are independently anionic ligands,
$L^1$ is a N-heterocyclic carbene ligand, and
$L^2$ is a phenylphosphine ligand, a tri(isopropoxy)phosphine ligand, a dimethylsulfoxide ligand, an acetonitrile ligand, or a pyridine ligand.

2. The method of claim 1, wherein the conjugated diene is an E,Z-diene.

3. The method claim 1, wherein the first carbene ligand is optionally substituted indenylidene, optionally substituted alkylidene, optionally substituted benzylidene, optionally substituted vinylidene, or optionally substituted allenylidene.

4. The method of claim 1, wherein $R^6$ and $R^7$, together with the carbon atom to which they are attached, form 3-phenyl-1H-inden-1-ylidene, benzylidene, or 3-methylbut-2-en-1-ylidene.

5. The method of claim 4, wherein $R^6$ and $R^7$, together with the carbon atom to which they are attached, form 3-phenyl-1H-inden-1-ylidene.

6. The method of claim 1, wherein $L^1$ is optionally substituted imidazolidin-2-ylidene.

7. The method of claim 1, wherein the metathesis catalyst is selected from:

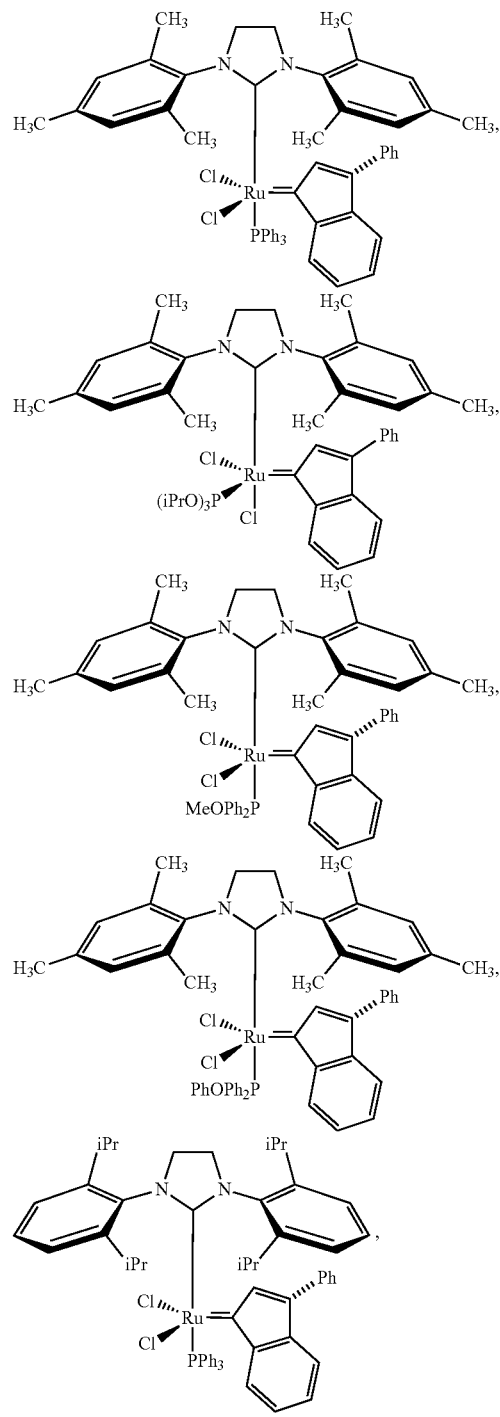

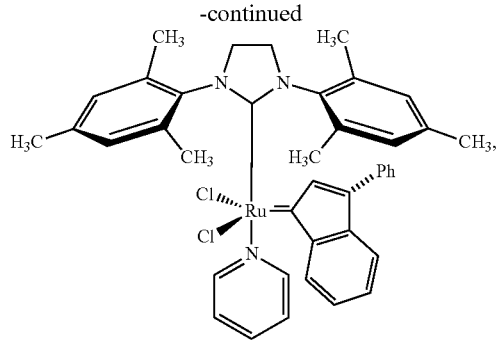
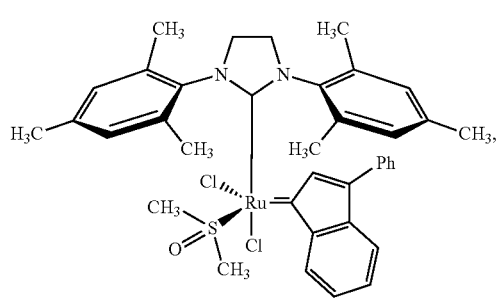
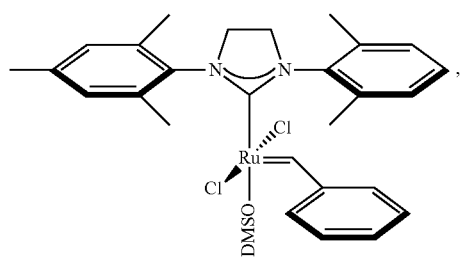
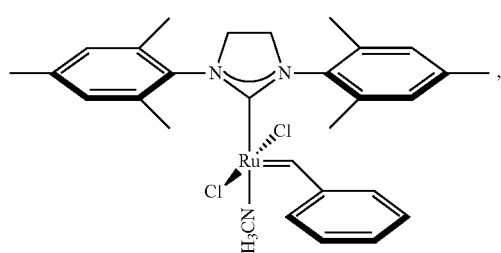
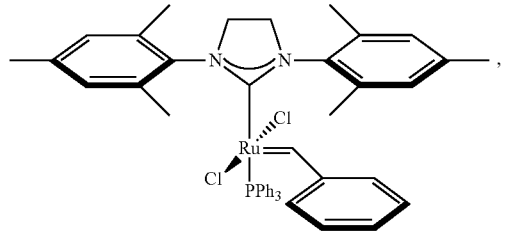
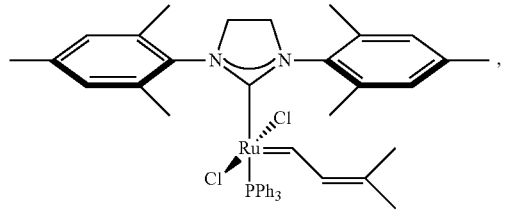
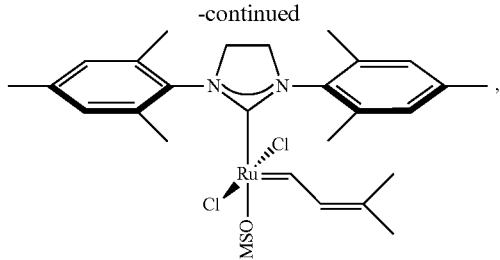
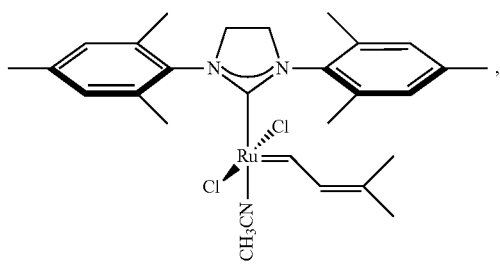
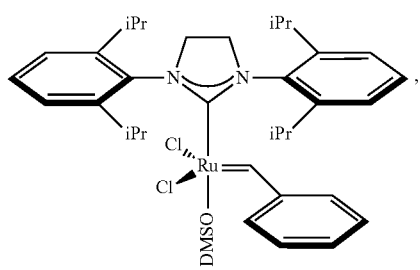
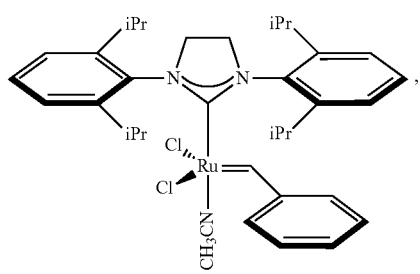
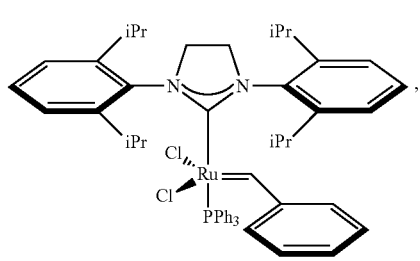
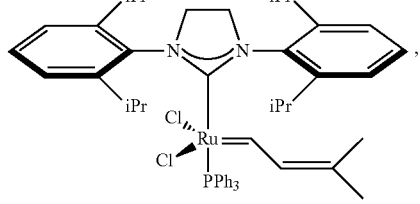

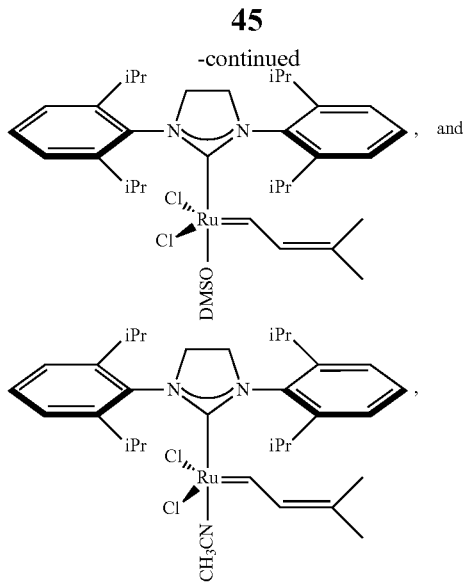

wherein "Ph" represents phenyl, "iPr" represents isopropyl, and DMSO represents dimethylsulfoxide.

8. The method of claim 1, wherein the amount of the metathesis catalyst in the reaction mixture is less than 0.05 mol % with respect to the total amount of olefin according to Formula V and the crotonaldehyde.

9. The method of claim 1, wherein the molar ratio of the crotonaldehyde to the olefin according to Formula V ranges from about 1.5:1 to about 3:1.

10. The method of claim 1, wherein the metathesis product according to Formula III of step (ii) is not purified prior to step (iii).

11. The method of claim 1, wherein the phosphonium ylide according to Formula II is formed by reacting a base with an alkylphosphonium halide according to Formula IIa

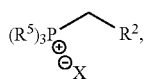

(IIa)

wherein X is halogen.

12. The method of claim 11, wherein the base is potassium tert-butoxide.

13. The method of claim 1, wherein the conjugated diene is selected from the group consisting of (7E,9Z)-dodeca-7,9-dien-1-yl acetate, (3E,5Z)-dodeca-3,5-dien-1-yl acetate, (3E,5Z)-dodeca-3,5-dien-1-yl acetate, (5E,7Z)-dodeca-5,7-dien-1-yl acetate, (8E,10Z)-dodeca-8,10-dien-1-yl acetate, (5E,7Z)-dodeca-5,7-dien-1-ol, (5E,7Z)-dodeca-5,7-dienal, (7E,9Z)-dodeca-7,9-dien-1-ol, (7E,9Z)-dodeca-7,9-dienal, (8E,10Z)-dodeca-8,10-dien-1-ol, (8E,10Z)-dodeca-8,10-dienal, (2E,4Z)-hepta-2,4-dien-1-ol, (2E,4Z)-hepta-2,4-dienal, (2E,4Z)-octa-2,4-dienal, (4E,6Z)-octa-4,6-dienoic acid, (2E,4Z)-deca-2,4-dienal, ethyl (2E,4Z)-deca-2,4-dienoate, (10E,12Z)-tetradeca-10,12-dien-1-yl acetate, (3E,5Z)-tetradeca-3,5-dienoic acid, (3E,5Z)-tetradeca-3,5-dien-1-yl acetate, (8E,10Z)-tetradeca-8,10-dienal, (8E,10Z)-tetradeca-8,10-dien-1-yl acetate, (9E,11Z)-tetradeca-9,11-dien-1-yl acetate, (6E,8Z)-pentadeca-6,8-dienal, (8E,10Z)-pentadeca-8,10-dien-1-ol, (8E,10Z)-pentadeca-8,10-dien-1-yl acetate, (9E,11Z)-pentadeca-9,11-dienal, (10E,12Z)-hexadeca-10,12-dien-1-ol, (10E,12Z)-hexadeca-10,12-dienal, (10E,12Z)-hexadeca-10,12-dien-1-yl acetate, (11E,13Z)-hexadeca-11,13-dien-1-ol, (11E,13Z)-hexadeca-11,13-dienal, (11E,13Z)-hexadeca-11,13-dien-1-yl acetate, (9E,11Z)-hexadeca-9,11-dienal, and (9E,11Z)-hexadeca-9,11-dien-1-yl acetate.

14. The method of claim 1, wherein the conjugated diene is (7E,9Z)-dodeca-7,9-dien-1-yl acetate.

15. The method of claim 1, wherein the metathesis product according to Formula III formed during step (ii) has a molar ratio of E olefin to Z olefin greater than 20:1.

16. The method of claim 1, wherein the conjugated diene according to Formula I formed during step (iii) has a molar ratio of Z olefin to E olefin greater than 8:1.

17. The method of claim 1, wherein:
the olefin according to Formula V is oct-7-en-1-yl acetate,
the metathesis product according to Formula III is E-9-oxonon-7-en-1-yl acetate,
the phosphonium ylide according to Formula II is triphenyl(propylidene)-25-phosphane, and
the conjugated diene is E,Z-dodeca-7,9-dien-1-yl acetate.

18. The method of claim 17, wherein the metathesis catalyst is 1,3-bis(2,4,6-trimethylphenyl)-2-imidazolidinylidene]dichloro(3-phenyl-1H-inden-1-ylidene)(triphenylphosphine)ruthenium (II):

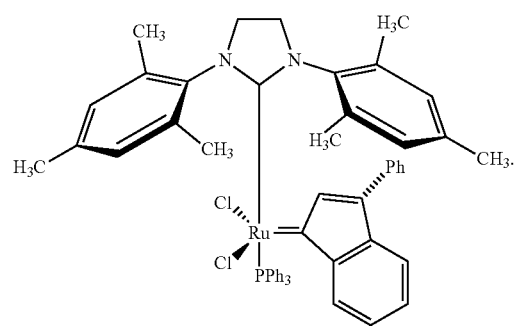

19. The method of claim 1, wherein the phenylphosphine ligand is a triphenylphosphine.

* * * * *